(12) United States Patent
Jetti et al.

(10) Patent No.: US 10,800,777 B2
(45) Date of Patent: Oct. 13, 2020

(54) POLYMORPHIC FORMS OF VENCLEXTA

(71) Applicant: Mylan Laboratories Limited, Hyderabad (IN)

(72) Inventors: Ramakoteswara Rao Jetti, Hyderabad (IN); Hemant Malhari Mande, Hyderabad (IN); Anjaneyaraju Indukuri, Hyderabad (IN); Narasimha Murthy Pilli, Hyderabad (IN); Rajesh Joshi, Hyderabad (IN); Anil Kumar Tripathi, Hyderabad (IN); Chandrakant Chaudhri, Hyderabad (IN); Kiran Pokharkar, Hyderabad (IN); Nagaraju Gottumukkala, Hyderabad (IN)

(73) Assignee: Mylan Laboratories Limited, Hyderabad (IN)

( * ) Notice: Subject to any disclaimer, the term of this patent is extended or adjusted under 35 U.S.C. 154(b) by 0 days.

(21) Appl. No.: 16/341,198

(22) PCT Filed: Oct. 13, 2017

(86) PCT No.: PCT/IN2017/050471
§ 371 (c)(1),
(2) Date: Apr. 11, 2019

(87) PCT Pub. No.: WO2018/069941
PCT Pub. Date: Apr. 19, 2018

(65) Prior Publication Data
US 2019/0233416 A1    Aug. 1, 2019

(30) Foreign Application Priority Data

Oct. 14, 2016   (IN) .............................. 201641035213
Oct. 28, 2016   (IN) .............................. 201641037144
Feb. 23, 2017   (IN) .............................. 201741006482

(51) Int. Cl.
*C07D 471/04*    (2006.01)

(52) U.S. Cl.
CPC ........ *C07D 471/04* (2013.01); *C07B 2200/13* (2013.01)

(58) Field of Classification Search
CPC ................................................... C07D 471/04
See application file for complete search history.

(56) References Cited

U.S. PATENT DOCUMENTS

| 8,546,399 B2 | 10/2013 | Bruncko et al. |
| 8,722,657 B2 | 5/2014 | Catron et al. |
| 2014/0275540 A1 | 9/2014 | Chan et al. |

FOREIGN PATENT DOCUMENTS

| CN | 107089981 A1 | 8/2017 |
| WO | 2012058392 A1 | 5/2012 |
| WO | 2012121758 A1 | 9/2012 |
| WO | 2014058392 A1 | 4/2014 |
| WO | 2017156398 A1 | 9/2017 |
| WO | 2017212431 A1 | 12/2017 |
| WO | 2018029711 A2 | 2/2018 |

OTHER PUBLICATIONS

Kakkar et al. Drug Development and industrial Pharmacy, 23(11), 1063-1067 (1997).*
PCT International Search Report for application PCT/IN2017/050471; dated May 30, 2018.
PCT Written Opinion of the International Searching Authority for application PCT/IN2017/050471, dated May 28, 2018.
David L. Hughes: "Patent Review of Manufacturing Routes to Oncology Drugs: Cartilzomib, Osimertinib, and Venetoclax", Organic Process Research and Development, vol. 20, No. 12, Dec. 16, 2016, pp. 2028-2042, XP055352183, US ISSN: 1083-6160, DOI: 10.1021/acs.oprd.6b00374.

* cited by examiner

*Primary Examiner* — Emily A Bernhardt

(57) ABSTRACT

The present disclosure relates to crystalline forms of venetoclax and process for their preparation. The present disclosure also relates to process for preparation of amorphous venetoclax.

2 Claims, 26 Drawing Sheets

POLYMORPHIC FORMS OF VENCLEXTA

CROSS-REFERENCE TO RELATED APPLICATIONS

This application is a national stage entry under 35 U.S.C. § 371 of International Application PCT/IN2017/050471 with an international filing date of Oct. 13, 2017, which claims the benefit of earlier Indian provisional patent application No. 201741006482, filed on Feb. 23, 2017; Indian provisional patent application No. 201641039093, filed on Nov. 16, 2016; Indian provisional patent application No. 201641037144, filed on Oct. 28, 2016; and Indian provisional patent application No. 201641035213, filed on Oct. 14, 2016 and incorporates the PCT and Indian applications into the current application by reference in their entirety.

BACKGROUND OF THE INVENTION

Field of the Invention

The present invention relates generally to pharmaceutically active compounds and more specifically to novel crystalline forms of venetoclax and processes for the preparation thereof.

Background of the Invention

Venetoclax (also called GDC-0199, ABT-199, and RG7601) is a BCL-2 inhibitor. Venetoclax is chemically known as 4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide and has the structure shown below as Formula-I:

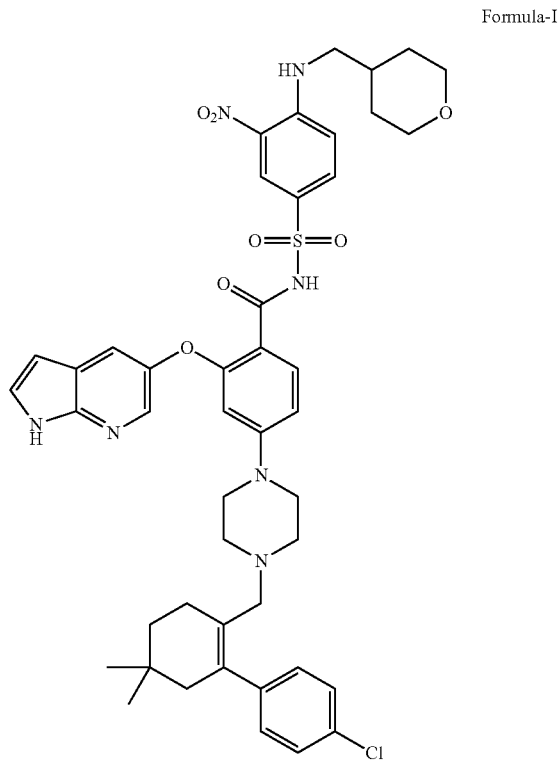 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

Formula-I

Venetoclax is marketed in the United States as VENCLEXTA™, which is indicated for the treatment of chronic lymphocytic leukemia.

U.S. Pat. No. 8,546,399, which is hereby incorporated by reference, discloses venetoclax and its preparation.

U.S. Pat. No. 8,722,657, which is hereby incorporated by reference, discloses anhydrous and hydrated crystalline forms A to N of venetoclax with characteristic powder X-ray diffraction data.

PCT Publication Nos. WO 2012/121758 and WO 2012/58392 disclose non-crystalline solid dispersions of venetoclax.

The inventors of the invention disclosed herein have developed novel crystalline forms of venetoclax, process for their preparation, and processes for the preparation of amorphous venetoclax.

SUMMARY OF THE INVENTION

In one aspect, the present invention provides venetoclax crystalline form M9 which, in one embodiment, may be characterized by a PXRD pattern having significant peaks at 2Θ angles of 6.31, 11.35, and 22.26±0.2°. In another embodiment, venetoclax crystal line form M9 may be characterized by a PXRD pattern having significant peaks at 2Θ angles of 6.31, 11.35, 13.26, 14.23, 16.76, 19.15, and 22.26±0.2°. In yet another embodiment, venetoclax crystalline form M9 may be characterized by the PXRD pattern as shown in FIG. 9.

In another aspect, the present invention provides a process for the preparation of venetoclax crystalline form M9. In one embodiment, venetoclax crystalline form M9 may be prepared by a process that includes the step of drying venetoclax crystalline form M1 at a temperature of about 110° C. to about 130° C. under vacuum for about 2 hours to about 4 hours.

In another embodiment, venetoclax crystalline form M9 may be prepared by a process that includes drying venetoclax crystalline form M22 at about 30° C. to about 80° C. for about 46 to about 50 hours.

In another aspect, the present invention provides venetoclax crystalline form M10, which, in one embodiment, may be characterized by a PXRD pattern having significant peaks at 2Θ angles of 19.90, 20.36, and 24.50±0.2°. In another embodiment, venetoclax crystalline form M10 may be characterized by a PXRD pattern having significant peaks at 2Θ angles of 9.65, 14.74, 19.38, 19.90, 20.36, 21.00, and 24.50±0.2°. In yet another embodiment, venetoclax crystalline form M10 may be characterized by a PXRD pattern as shown in FIG. 10.

In another aspect, the present invention provides a process for the preparation of venetoclax crystalline form M10. In one embodiment, venetoclax crystalline form M10 may be prepared by a process that includes the step of drying venetoclax crystalline form M4 at about 140° C. to 170° C. under vacuum for about 2 to about 4 hours.

In another aspect, the present invention provides venetoclax crystalline form M21, which, in one embodiment, may be characterized by a PXRD pattern having significant peaks at 2Θ angles of 18.80, 19.10, and 21.67±0.2°. In another embodiment venetoclax crystalline form M21 may be characterized by a PXRD pattern having significant peaks at 2Θ angles of 15.59, 15.87, 16.13, 18.80, 19.10, 19.47, and 21.67±0.2°.

In another aspect, the present invention provides a process for the preparation of venetoclax crystalline form M21. In one embodiment, venetoclax crystalline form M21 may be prepared by a process that includes the steps of:
a) dissolving venetoclax in an organic solvent at about 100° C. to about 110° C. to form a solution;
b) cooling the solution to about 65° C. to about 80° C.;
C) optionally adding seeds of venetoclax form M21; and
d) isolating venetoclax crystalline form M21.

Within the context of this embodiment, the organic solvent may be N-butyl acetate, toluene, or mixtures thereof.

In another aspect, the present invention provides a process for preparing amorphous venetoclax. In one embodiment, amorphous venetoclax may be prepared by a process that includes the steps of:
a) dissolving venetoclax in an organic solvent to form a solution;
b) combining the solution with an anti-solvent; and
c) isolating amorphous venetoclax.

Within the context of this embodiment, the organic solvent may be, for example, dichloromethane, tetrahydrofuran, toluene, ethyl acetate, acetonitrile, acetone, dimethylformamide, dimethylsulfoxide, N-methylpyrrolidone, sulfolane, or mixtures thereof.

Within the context of this embodiment, the anti-solvent is water.

In another embodiment, amorphous venetoclax may be prepared by a process that includes the step of drying venetoclax crystalline form M20 at a temperature from about 60° C. to about 80° C. for about 15 hours to about 25 hours.

BRIEF DESCRIPTION OF THE FIGURES

Further aspects of the present invention together with additional features contributing thereto and advantages accruing there from will be apparent from the following description of embodiments of the disclosure which are shown in the accompanying drawing figures wherein.

DETAILED DESCRIPTION OF THE INVENTION

Within the context of the invention, the term "about" when modifying an absolute measurement, such as time, mass, or volume, is meant to mean the recited value plus or minus 10% of that value. Within the context of the invention, the term "about" when modifying a temperature measurement is meant to mean the recited temperature plus or minus five degrees.

The present invention provides new polymorphs of venetoclax which may be characterized by powder X-ray diffraction (PXRD). Thus, samples of each disclosed polymorph were analyzed by PXRD on a BRUKER D-8 Discover powder diffractometer equipped with a goniometer of θ/2θ configuration and Lynx Eye detector. The Cu-anode X-ray tube was operated at 40 kV and 30 mA. The experiments were conducted over the 2θ range of 2.0°-50.0°, 0.030° step size, and 0.4 seconds step time.

In one aspect, the present invention provides venetoclax crystalline form M1.

Figure 1:
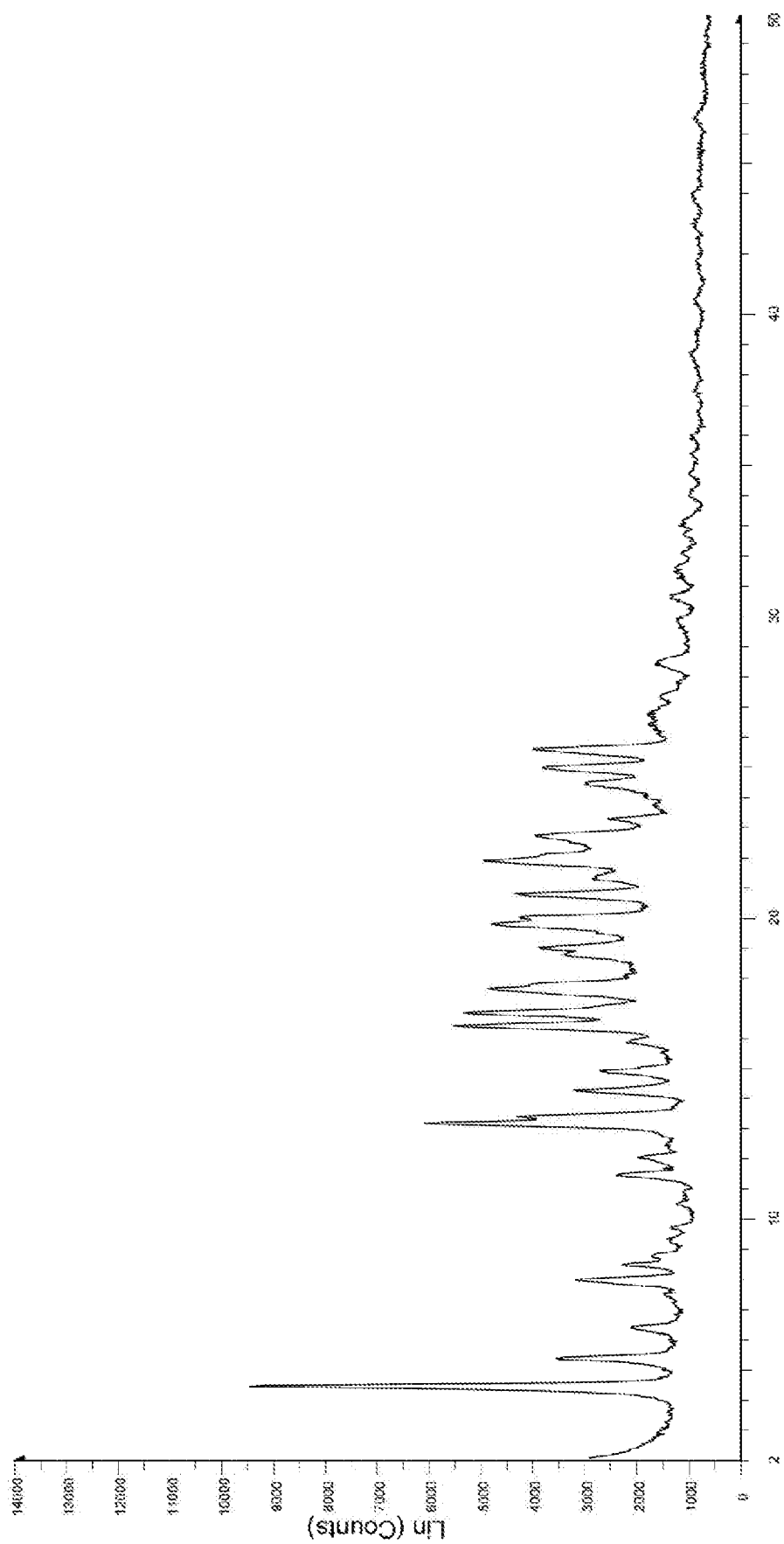
FIG. 1 is an X-ray powder diffractogram of venetoclax crystalline form M1.

Within the context of the present invention, venetoclax crystalline form M1 may be characterized by a PXRD pattern having significant peaks at 2Θ angles of 4.39, 5.31, 6.34, 7.92, 8.43, 11.41, 12.00, 13.11, 13.37, 14.21, 14.85, 15.86, 16.38, 16.82, 17.60, 18.75, 18.96, 19.75, 19.96, 20.75, 21.30, 21.86, 22.69, 23.26, 24.42, 24.96, 25.56, 26.75, and 28.43±0.2°. A representative PXRD pattern for venetoclax crystalline form M1 is shown in FIG. 1.

In another aspect, the present invention provides a process for the preparation of venetoclax crystalline form M1. In one embodiment, venetoclax crystalline form M1 may be prepared by a process that includes the steps of:
a) dissolving venetoclax in isobutyl acetate at about 60° C. to about 85° C. to form a solution;
b) cooling the solution to about 15° C. to about 35° C.;
c) optionally adding an anti-solvent; and
d) isolating venetoclax crystalline form M1.

Within the context of this embodiment, venetoclax may be dissolved in isobutyl acetate at about 60° C. to about 85° C. This range includes temperatures of 60° C., 65° C., 70° C., 75° C., 80° C., 85° C., and any temperature between any of those aforementioned, including 60° C.-65° C., 60° C.-70° C., 60° C.-75° C., 60° C.-80° C., 65° C.-70° C., 65°

C.-75° C., 65° C.-80° C., 65° C.-85° C., 70° C.-75° C., 70° C.-80° C., 70° C.-85° C., 75° C.-80° C., 75° C.-85° C., and 80° C.-85° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may be added. Venetoclax crystalline form M1 may then be isolated.

Within the context of this embodiment, the anti-solvent may be an ether solvent, for example, but not limited to, methyl tert-butyl ether, diisopropyl ether, diethyl ether, or mixtures thereof.

Isolation of venetoclax crystalline form M1 may be carried out by methods well-known and often used in the art, for example, by filtering the mixture to obtain a solid.

It is believed that venetoclax crystalline form M1 is a solvate of isobutyl acetate.

Figure 2:
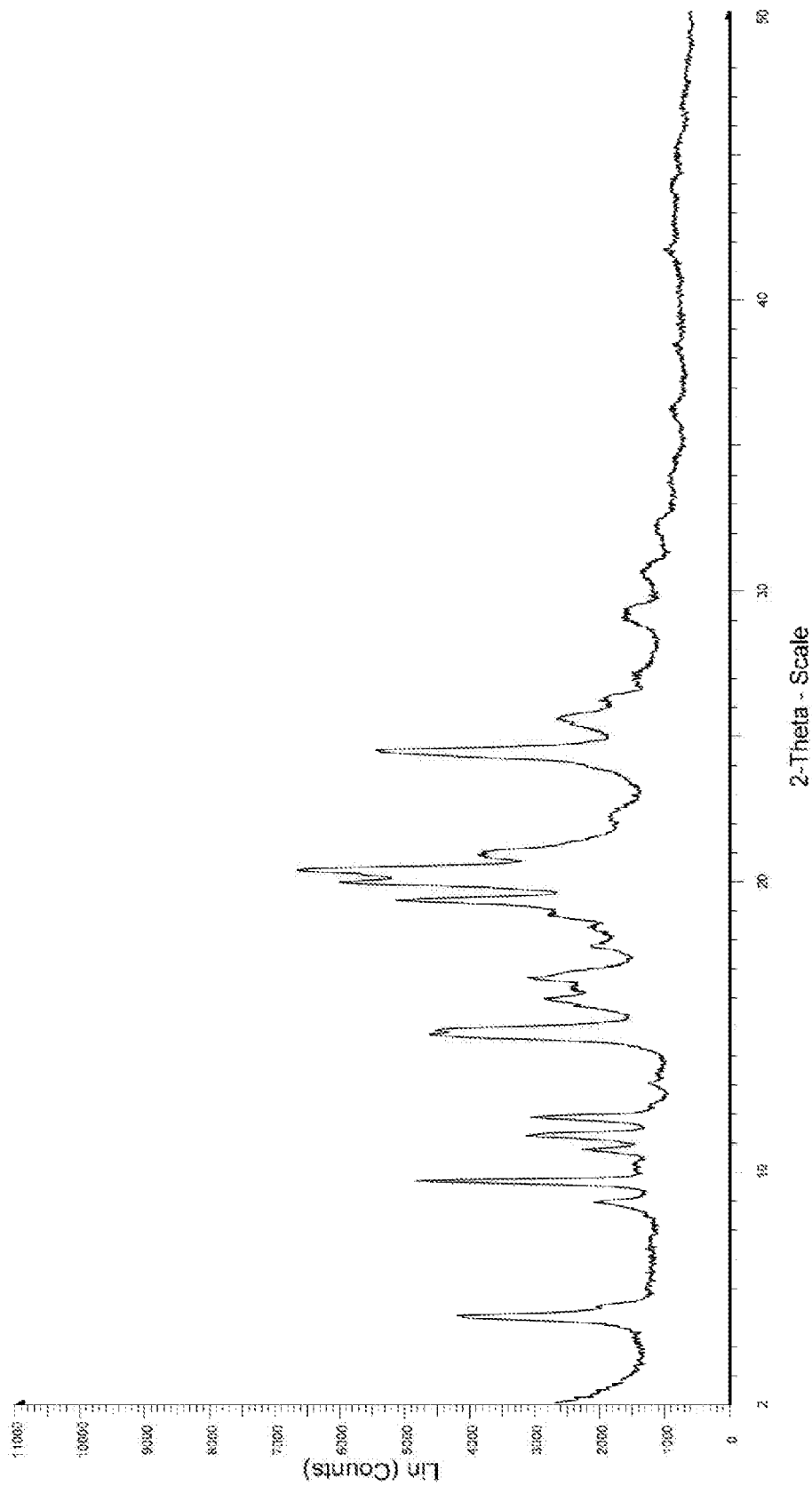
FIG. 2 is an X-ray powder diffractogram of venetoclax crystalline form M2.

In another embodiment, the present invention provides venetoclax crystalline form M2 characterized by a PXRD pattern having significant peaks at 2Θ angles of 4.97, 5.35, 8.91, 9.63, 10.71, 11.21, 11.83, 14.80, 15.90, 16.31, 16.63, 17.75, 18.39, 18.83, 19.31, 19.95, 20.36, 20.88, 22.16, 24.47, 25.61, 26.26, 26.87, 29.07, 29.33, and 30.64±0.2°. A representative PXR D pattern for venetoclax crystalline form M2 is shown in FIG. 2.

In another aspect, the present invention provides a process for the preparation of venetoclax crystalline form M2. In one embodiment, venetoclax crystalline form M2 may be prepared by a process that includes the steps of:
a) dissolving venetoclax in anisole at about 60° C. to about 85° C. to form a solution;
b) cooling the solution to about 15° C. to about 35° C.;
c) optionally adding an anti-solvent; and
d) isolating venetoclax crystalline form M2.

According to the present embodiment, venetoclax may be dissolved in anisole at about 60° C. to about 85° C. to form a solution. This range includes temperatures of 60° C., 65° C., 70° C., 75° C., 80° C., 85° C., and any temperature between any of those aforementioned, including 60° C.-65° C., 60° C.-70° C., 60° C.-75° C., 60° C.-80° C., 65° C.-70° C., 65° C.-75° C., 65° C.-80° C., 65° C.-85° C., 70° C.-75° C., 70° C.-80° C., 70° C.-85° C., 75° C.-80° C., 75° C.-85° C., and 80° C.-85° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may be added. Venetoclax crystalline form M2 may then be isolated.

Within the context of this embodiment, anti-solvent is hydrocarbon solvent, which may be, for example, pentane, hexane, cyclohexane, methyl cyclohexane, heptane, 2-methyl pentane, ethyl cyclohexane, or mixtures thereof.

Isolation of venetoclax crystalline form M2 may be carried out by methods well-known and often used in the art, for example, by filtering the mixture to obtain a solid.

It is believed that venetoclax crystalline form M2 may be an anisole solvate.

Figure 3:
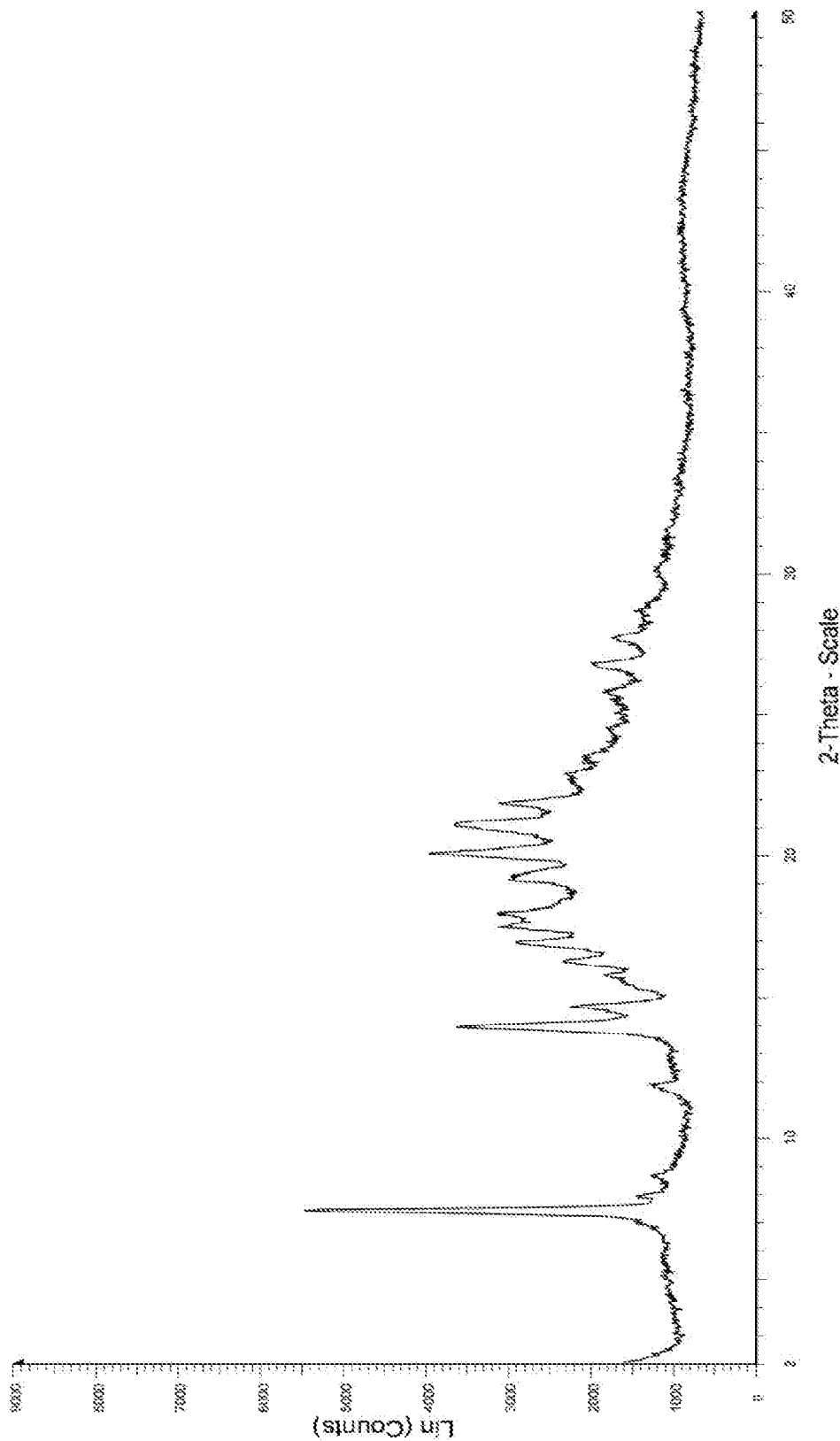
FIG. 3 is an X-ray powder diffractogram of venetoclax crystalline form M3.

In another embodiment, the present invention provides venetoclax crystalline form M3, which may be characterized by a PXRD pattern having significant peaks at 2Θ angles of 7.36, 7.88, 11.82, 13.92, 14.64, 15.49, 15.72, 16.23, 16.90, 17.50, 17.92, 19.96, 20.06, 21.10, 21.85, 22.94, 23.60, 24.49, 25.51, 25.80, 26.77, 27.72, and 28.66±0.2°. A representative PXRD pattern for venetoclax crystalline form M3 is shown in FIG. 3.

In another aspect, the present invention provides a process for the preparation of venetoclax crystalline form M3. In one embodiment, venetoclax crystalline form M3 may be prepared by a process that includes the steps of:
a) dissolving venetoclax in acetonitrile at about 60° C. to about 80° C. to form a solution;
b) cooling the solution to about 15° C. to about 35° C.;
c) optionally adding an anti-solvent; and
d) isolating venetoclax crystalline form M3.

According to the present embodiment, venetoclax may be dissolved in acetonitrile at about 60° C. to about 80° C. This range includes temperatures of 60° C., 65° C., 70° C., 75° C., 80° C., and any temperature between any of those aforementioned, including 60° C.-65° C., 60° C.-70° C., 60° C.-75° C., 65° C.-70° C., 65° C.-75° C., 65° C.-80° C., 70° C.-75° C., 70° C.-80° C., and 75° C.-80° C. The solution may then be cooled to about 15° C. to about 35° C., which includes 15° C., 20° C., 25° C., 30° C., 35° C., an d any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 to about 3 hours. Optionally, an anti-solvent may then be added. Venetoclax crystalline form M3 may then be isolated.

Within the context of the present embodiment, anti-solvent may be hydrocarbon solvent, which may be, for example, pentane, hexane, cyclohexane, methyl cyclohexane, heptane, 2-methyl pentane, ethyl cyclohexane, or mixtures thereof.

Isolation of venetoclax crystalline form M3 may be carried out by methods well-known and often used in the art, for example, by filtering the mixture to obtain a solid.

It is believed that venetoclax crystalline form M3 is an acetonitrile solvate.

Figure 4:
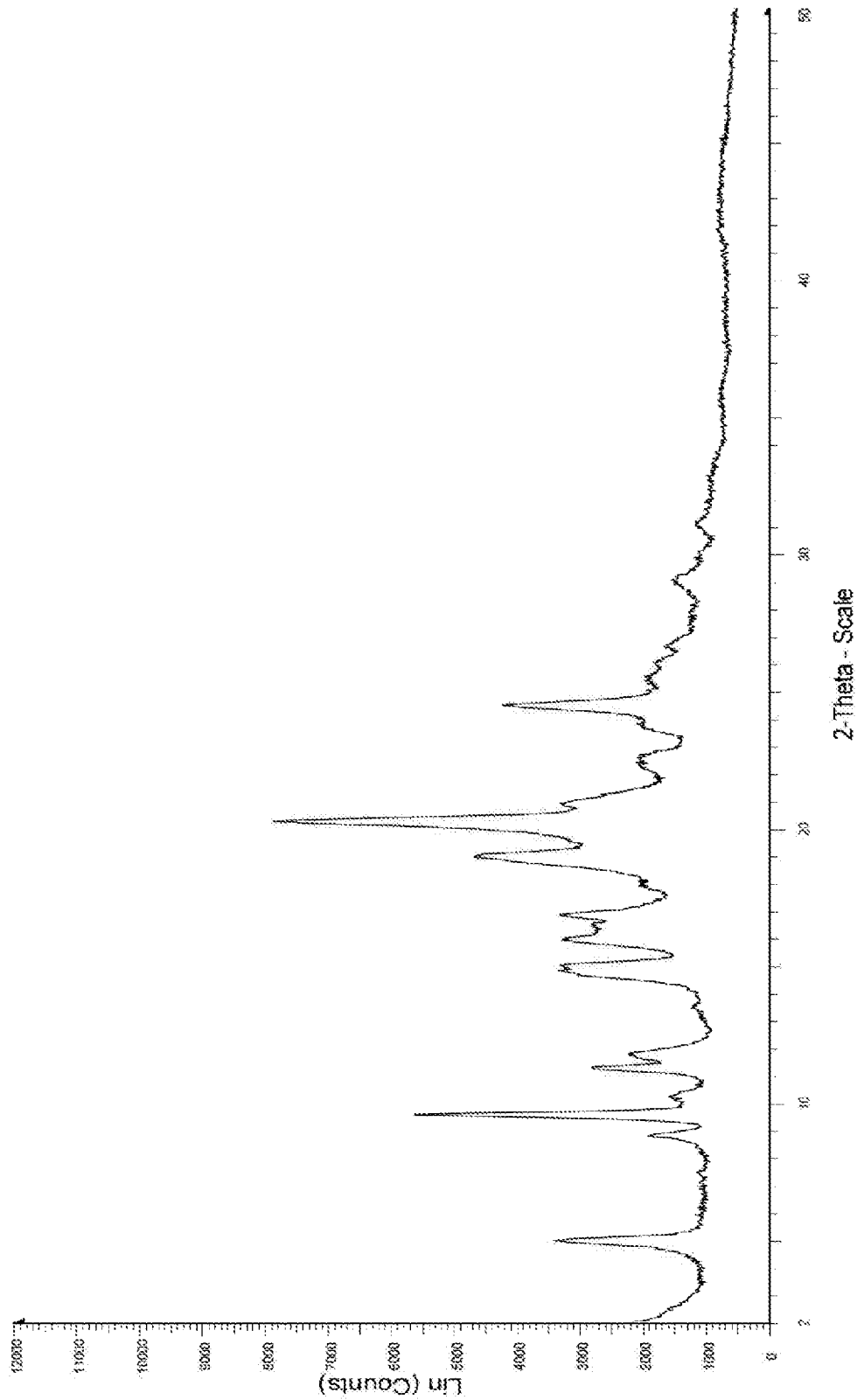
FIG. 4 is an X-ray powder diffractogram of venetoclax crystalline form M4.

In another embodiment, the present invention provides venetoclax crystalline form M4 characterized by a PXRD pattern having significant peaks at 2Θ angles of 4.96, 8.81, 9.55, 11.25, 11.76, 14.85, 14.99, 15.96, 16.43, 16.85, 17.98, 19.01, 20.28, 20.91, 22.54, 23.82, 24.51, 25.47, 26.03, 26.67, and 29.07±0.2°. A representative PXRD pattern for venetoclax crystalline form M4 is shown in FIG. 4.

In another aspect, the present invention provides a process for the preparation of venetoclax crystalline form M4. In one embodiment, venetoclax crystalline form M4 may be prepared by a process that includes the steps of:
a) dissolving venetoclax in toluene at about 60° C. to about 85° C. to form a solution;
b) cooling the solution to about 15° C. to about 35° C.;
c) optionally adding an anti-solvent; and
d) isolating venetoclax crystalline form M4.

According to the present embodiment, venetoclax may be dissolved in toluene at about 60° C. to about 85° C. This range includes temperatures of 60° C., 65° C., 70° C., 75° C., 80° C., 85° C., and any temperature between any of those aforementioned, including 60° C.-65° C., 60° C.-70° C., 60° C.-75° C., 60° C.-80° C., 65° C.-70° C., 65° C.-75° C., 65° C.-80° C., 65° C.-85° C., 70° C.-75° C., 70° C.-80° C., 70° C.-85° C., 75° C.-80° C., 75° C.-85° C., and 80° C.-85° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20°

C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may then be added. Venetoclax crystalline form M4 may then be isolated.

Within the context of the present embodiment, anti-solvent may be an ether solvent, which may be, for example, methyl tert-butyl ether, diisopropyl ether, diethyl ether, or mixtures thereof.

Isolation of venetoclax crystalline form M4 may be carried out by methods well known and often used in the art, for example, by filtering the mixture to obtain a solid.

It is believed that venetoclax crystalline form M4 is a toluene solvate.

Figure 5:
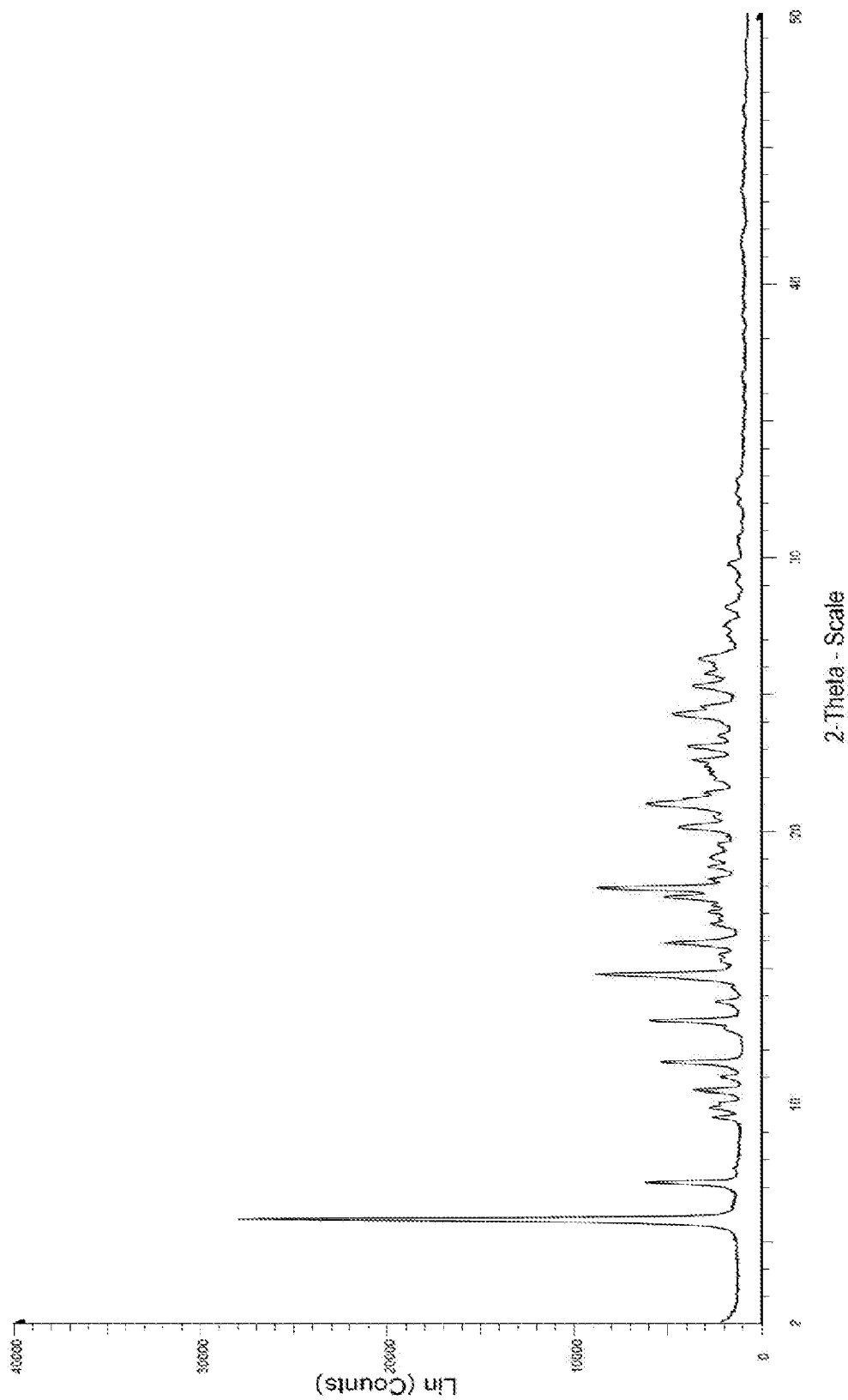
FIG. 5 is an X-ray powder diffractogram of venetoclax crystalline form M5.

In another embodiment, the present invention provides venetoclax crystalline form M5, which may be characterized by a PXRD pattern having significant peaks at 2Θ angles of 5.76, 7.10, 11.50, 13.03, 14.74, 15.88, 17.57, 17.91, 20.14, 20.98, 22.59, 23.09, 24.27, and 25.28±0.2°. A representative PXRD pattern for venetoclax crystalline form M5 is shown in FIG. 5.

In another aspect, the present invention provides a process for the preparation of venetoclax crystalline form M5. In one embodiment, venetoclax crystalline form M5 may be prepared by a process that includes the steps of:
 a) dissolving venetoclax in 3-pentanone at about 60° C. to about 85° C. to form a solution;
 b) cooling the solution to about 15° C. to about 35° C.;
 c) optionally adding an anti-solvent; and
 d) isolating venetoclax crystalline form M5.

According to the present embodiment, venetoclax may be dissolved in 3-pentanone at about 60° C. to about 85° C. This range includes temperatures of 60° C., 65° C., 70° C., 75° C., 80° C., 85° C., and any temperature between any of those aforementioned, including 60° C.-65° C., 60° C.-70° C., 60° C.-75° C., 60° C.-80° C., 65° C.-70° C., 65° C.-75° C., 65° C.-80° C., 65° C.-85° C., 70° C.-75° C., 70° C.-80° C., 70° C.-85° C., 75° C.-80° C., 75° C.-85° C., and 80° C.-85° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may then be added. Venetoclax crystalline form M5 may then be isolated.

Within the context of the present embodiment, the anti-solvent may be a hydrocarbon solvent, which may be, for example, pentane, hexane, cyclohexane, methyl cyclohexane, heptane, 2-methyl pentane, ethyl cyclohexane, or mixtures thereof.

Isolation of venetoclax crystalline form M5 may be carried out by methods well-known and often used in the art, for example, by filtering the mixture to obtain a solid.

It is believed that venetoclax crystalline form M5 is a 3-pentanone solvate.

Figure 6:
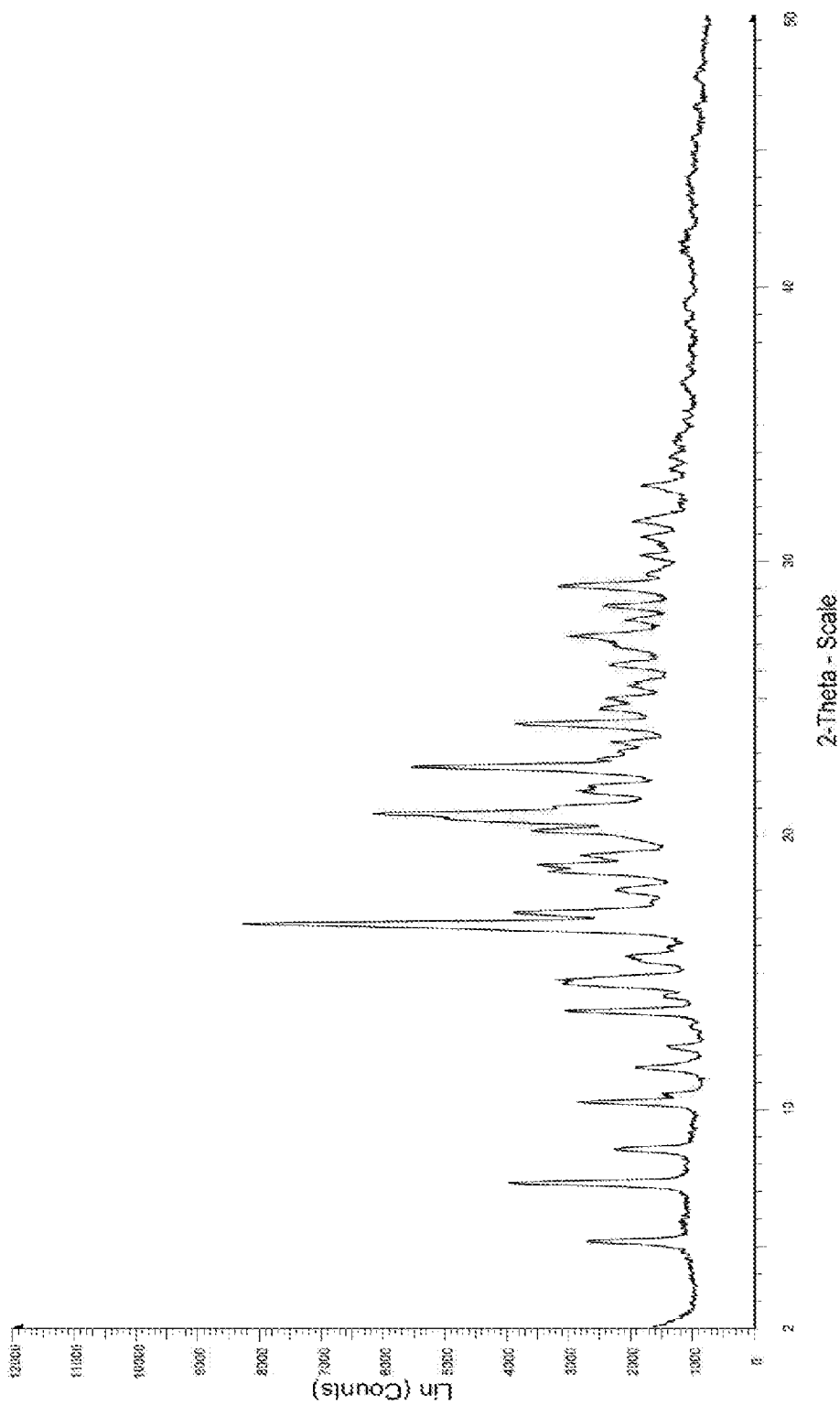
FIG. 6 is an X-ray powder diffractogram of venetoclax crystalline form M6.

In another embodiment, the present invention provides venetoclax crystalline form M6, which may be characterized by a PXRD pattern having significant peaks at 2Θ angles of 5.13, 7.24, 8.49, 10.22, 11.50, 13.57, 14.58, 14.70, 15.56, 16.74, 17.15, 17.99, 18.68, 18.90, 19.25, 20.16, 20.57, 20.78, 21.04, 21.59, 21.82, 22.48, 22.78, 23.37, 24.06, 24.62, 24.99, 25.44, 26.22, 26.95, 27.27, 27.86, 28.27, 29.10, 29.54, 30.21, 30.88, 31.47 and 32.80±0.2°. A representative PXRD pattern for venetoclax crystalline form M6 is shown in FIG. 6.

In another aspect, the present invention provides a process for the preparation of venetoclax crystalline form M6. In one embodiment, venetoclax crystalline form M6 may be prepared by a process that includes the steps of:
 a) dissolving venetoclax in dimethylformamide at about 60° C. to about 85° C. to form a solution;
 b) cooling the solution to about 15° C. to about 35° C.;
 c) optionally adding an anti-solvent; and
 d) isolating venetoclax crystalline form M6.

According to the present embodiment, venetoclax may be dissolved in dimethylformamide at about 60° C. to about 85° C. This range includes temperatures of 60° C., 65° C., 70° C., 75° C., 80° C., 85° C., and any temperature between any of those aforementioned, including 60° C.-65° C., 60° C.-70° C., 60° C.-75° C., 60-80° C., 65° C.-70° C., 65-75° C., 65° C.-80° C., 65° C.-85° C., 70° C.-75° C., 70° C.-80° C., 70° C.-85° C., 75° C.-80° C., 75° C.-85° C., and 80° C.-85° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may then be added. Venetoclax crystalline form M6 may then be isolated.

Within the context of the present embodiment, the anti-solvent may be a hydrocarbon solvent, which may be, for example, pentane, hexane, cyclohexane, methyl cyclohexane, heptane, 2-methyl pentane, ethyl cyclohexane, or mixtures thereof.

Isolation of venetoclax crystalline form M6 may be carried out by methods well known and often used in the art, for example, by filtering the mixture to obtain a solid.

It is believed that venetoclax crystalline form M6 is a dimethylformamide solvate.

Figure 7:
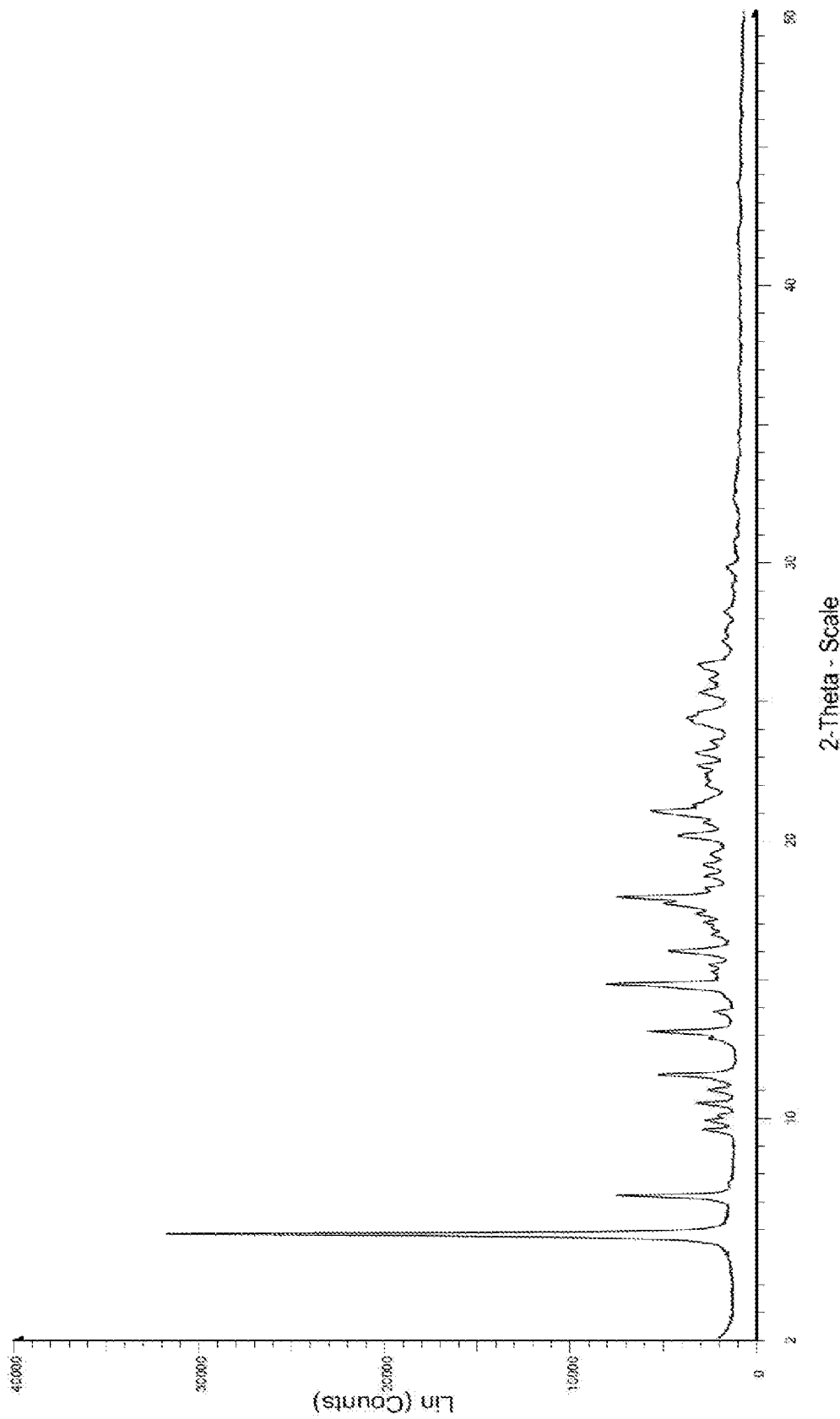
FIG. 7 is an X-ray powder diffractogram of venetoclax crystalline form M7.

In another embodiment, the present invention provides venetoclax crystalline form M7 characterized by a PXRD pattern having significant peaks at 2Θ angles of 5.77, 7.14, 11.52, 13.07, 14.77, 15.98, 17.69, 17.93, 20.16 and 21.03±0.2°. A representative PXRD pattern for venetoclax crystalline form M7 is shown in FIG. 7.

In another aspect, the present invention provides a process for the preparation of venetoclax crystalline form M7. In one embodiment, venetoclax crystalline form M7 may be prepared by a process that includes the steps of:
 a) dissolving venetoclax in methyl ethyl ketone at about 60° C. to about 85° C. to form a solution;
 b) cooling the solution to about 15° C. to about 35° C.;
 c) optionally adding an anti-solvent; and
 d) isolating venetoclax crystalline form M7.

According to the present embodiment, venetoclax may be dissolved in methyl ethyl ketone at about 60° C. to about 85° C. This range includes temperatures of 60° C., 65° C., 70° C., 75° C., 80° C., 85° C., and any temperature between any of those aforementioned, including 60° C.-65° C., 60° C.-70° C., 60° C.-75° C., 60° C.-80° C., 65° C.-70° C., 65° C.-75° C., 65° C.-80° C., 65° C.-85° C., 70° C.-75° C., 70° C.-80° C., 70° C.-85° C., 75° C.-80° C., 75° C.-85° C., and 80° C.-85° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15°

C.-30° C., 20° C.-25° C., 20° C.-30° C., 20° C.-35° C., 25° C.-30° C., 25° C.-35° C., and 30° C.-35° C. In some embodiments, cooling is carried out for about 2 hours to about 3 hours. Optionally, an anti-solvent may then be added. Venetoclax crystalline form M7 may then be isolated.

Within the context of the present embodiment, the anti-solvent may be an ether solvent, which may be, for example, methyl tert-butyl ether, diisopropyl ether, diethyl ether, or mixtures thereof.

Isolation of venetoclax crystalline form M7 may be carried out by methods well known and often used in the art, for example, by filtering the mixture to obtain a solid.

It is believed that venetoclax crystalline form M7 is a methyl ethyl ketone solvate.

Figure 8:
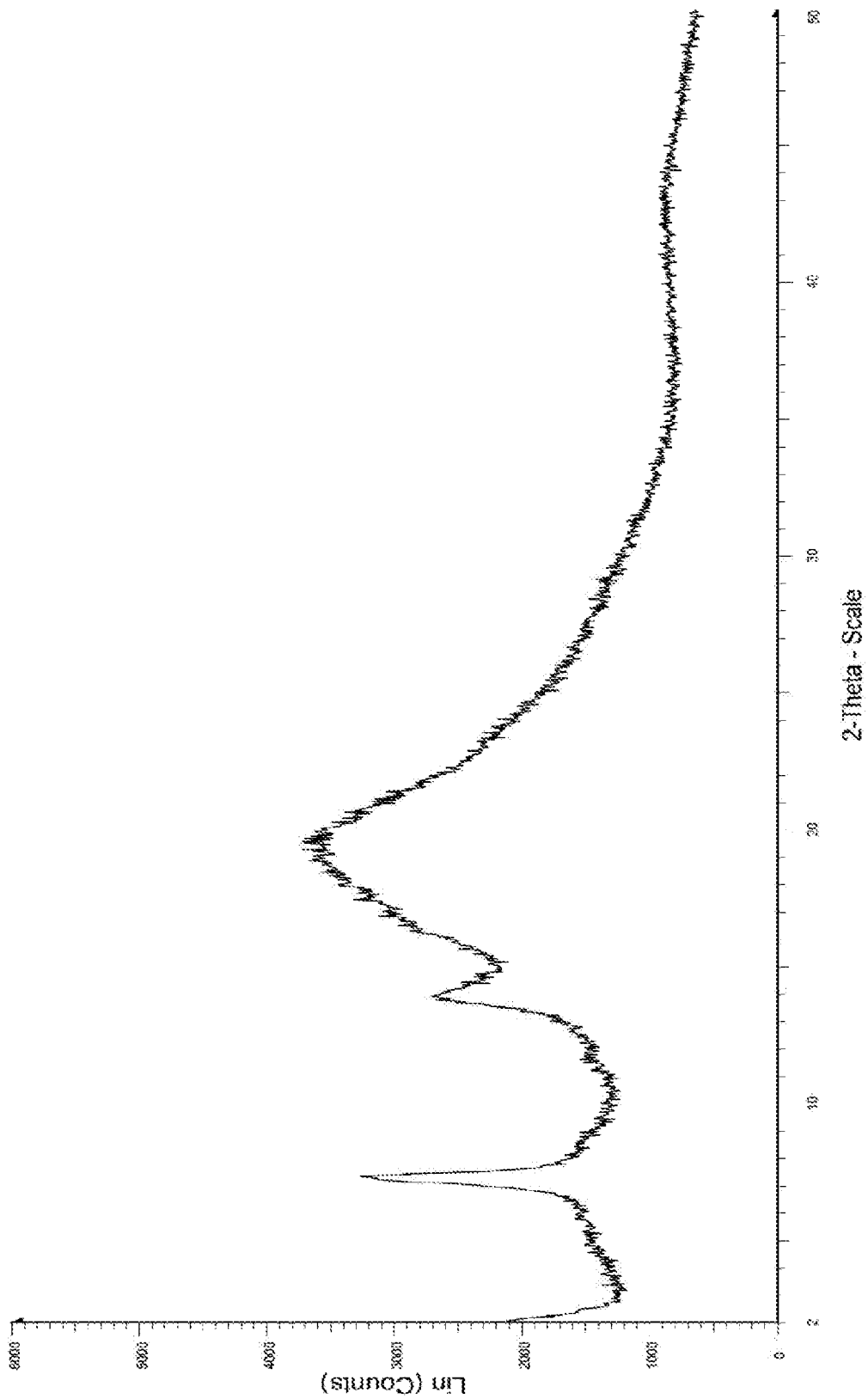
FIG. 8 is an X-ray powder diffractogram of venetoclax crystalline form M8.

In another embodiment, the present invention provides venetoclax crystalline form M8 characterized by a PXRD pattern having significant peaks at 2Θ angles of 7.28 and 13.86±0.2°. A representative PXRD pattern for venetoclax crystalline form M8 is shown in FIG. 8.

In another aspect, the present invention provides a process for the preparation of venetoclax crystalline form M8. In one embodiment, venetoclax crystalline form M8 may be prepared by a process that includes the steps of:
a) dissolving venetoclax in acetonitrile at about 60° C. to about 80° C. to form a solution;
b) distilling out approximately 90% of the solvent to result in a reaction mass;
c) cooling the reaction mass to about −5° C. to 10° C.; and
d) isolating venetoclax crystalline form M8.

According to the present embodiment, venetoclax may be dissolved in acetonitrile at about 60° C. to about 80° C. This range includes temperatures of 60° C., 65° C., 70° C., 75° C., 80° C., and any temperature between any of those aforementioned, including 60° C.-65° C., 60° C.-70° C., 60° C.-75° C., 65° C.-70° C., 65° C.-75° C., 65° C.-80° C., 70° C.-75° C., 70° C.-80° C., and 75° C.-80° C. In some embodiments, this dissolving step is carried out over the course of about 1 hour to about 2 hours. The solution may then be distilled to remove 90% of the solvent to result in a reaction mass. In some embodiments, distillation is carried out at a temperature of about 70° C. to about 75° C. In particularly useful embodiments, prior to distillation, the solution is filtered to remove any undissolved particles. In such embodiments, it may be particularly useful to filter at about 70° C. The reaction mass may then be cooled to about −5° C. to 10° C., which includes temperatures of −5° C., 0° C., 5° C., 10° C., and any temperature between these aforementioned temperatures including the ranges of −5° C.-0° C., −5° C.-5° C., 0° C.-5° C., 0° C.-10° C., and 5° C.-10° C. In particularly useful embodiments, the reaction mass is stirred for an extended period of time, for example, for about 4 to 5 hours.

Venetoclax crystalline form M8 may then be isolated.

Isolation of venetoclax crystalline form M8 may be carried out by methods well known and often used in the art, for example, by filtering the mixture to obtain a solid.

It is believed that venetoclax crystalline form M8 is an acetonitrile solvate.

In another aspect, the present invention provides venetoclax crystalline form M9, which may be characterized by a PXRD pattern having significant peaks at 2Θ angles of 6.31, 11.35, and 22.26±0.2°.

Figure 9:
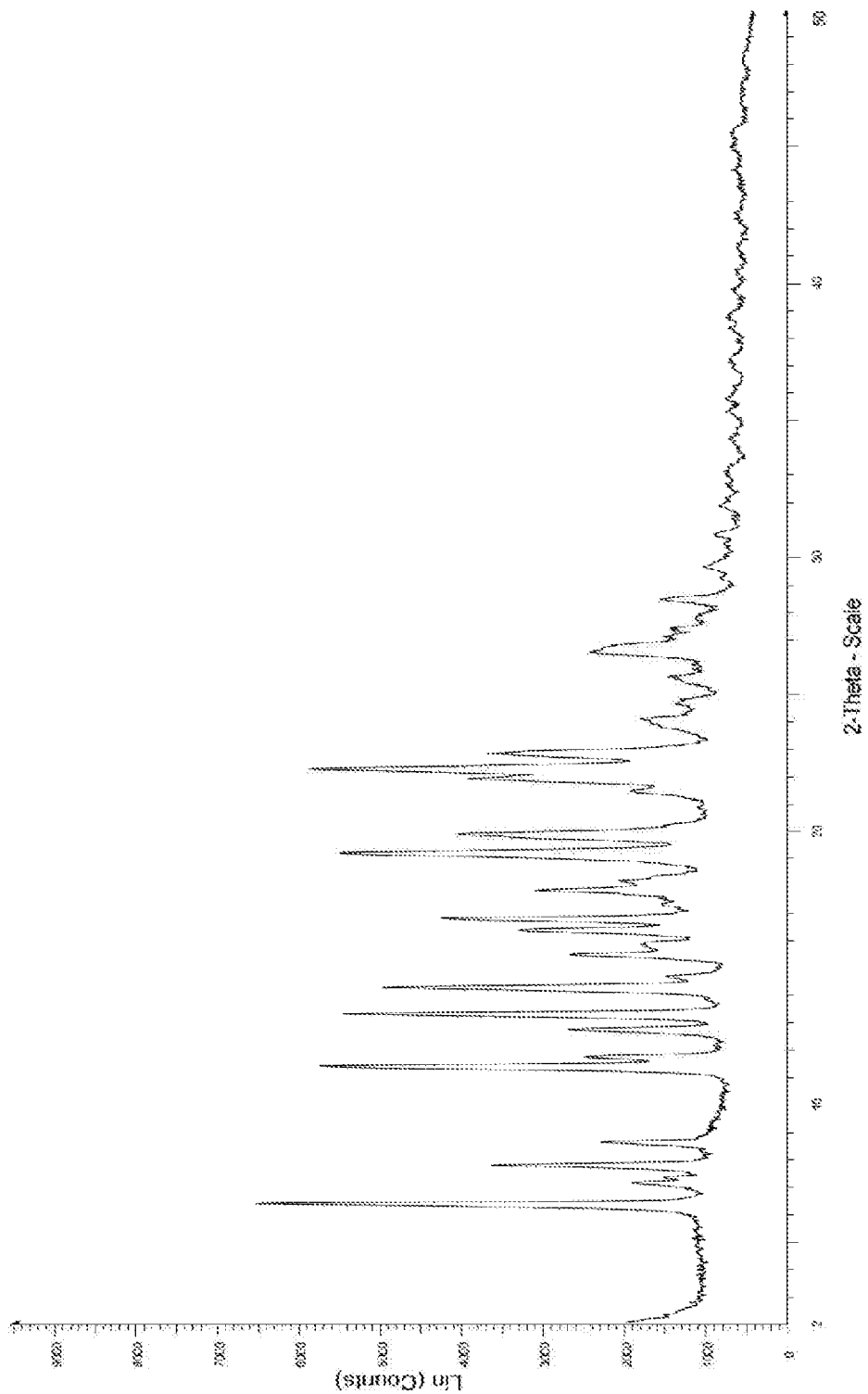
FIG. 9 is an X-ray powder diffractogram of venetoclax crystalline form M9.
Figure 24:
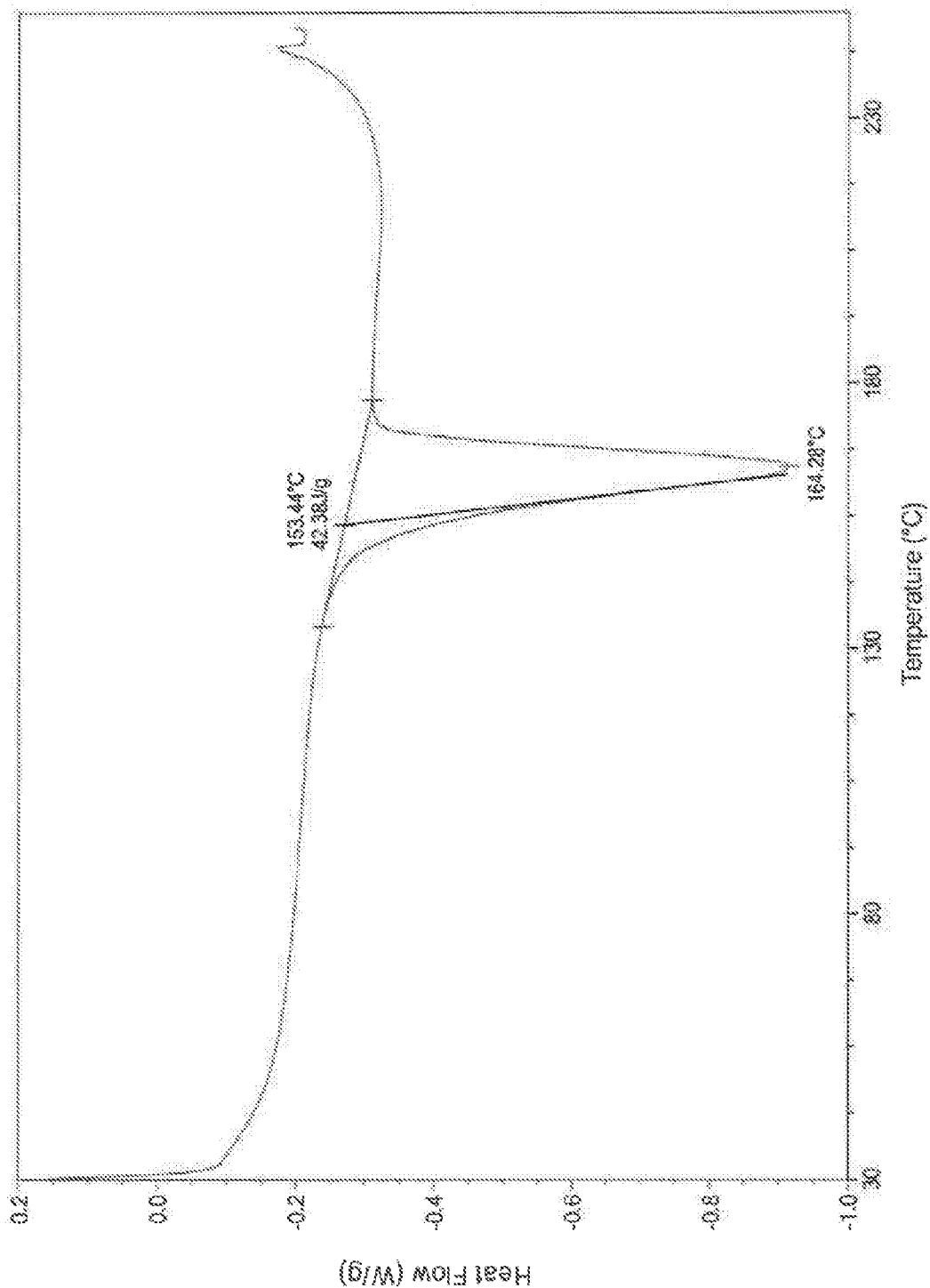
FIG. 24 is a differential scanning calorimetry (DSC) thermogram of venetoclax crystalline form M9.

In another embodiment, the present invention provides venetoclax crystalline form M9, which may be further characterized by a PXRD pattern having significant peaks at 2Θ angles of 6.31, 11.35, 13.26, 19.15, and 22.83±0.2°. Venetoclax crystalline form M9 may be further characterized by a PXRD pattern having significant peaks at 2Θ angles of 6.31, 7.09, 7.30, 7.73, 8.57, 11.35, 11.69, 12.69, 13.26, 14.23, 14.62, 15.44, 15.83, 16.33, 16.76, 17.27, 17.45, 17.79, 18.12, 18.24, 19.15, 19.87, 21.45, 21.92, 22.26, 22.83, 24.07, 24.67, 25.62, 26.54, 26.69, 27.09, 27.39 and 28.46±0.2°. A representative PXRD pattern for venetoclax crystalline form M9 is shown in FIG. 9. A representative differential scanning calorimetry (DSC) thermogram of venetoclax crystalline form M9 is shown in FIG. 24.

In another aspect, the present invention provides a process for the preparation of venetoclax crystalline form M9. In one embodiment, venetoclax crystalline form M9 may be prepared by a process that includes the step of drying venetoclax crystalline form M1 at about 110° C. to 130° C. under vacuum for about 2 to 4 hours. Within the context of this embodiment, this temperature range includes the temperatures of 110° C., 115° C., 120° C., 125° C., 130° C. and any temperature between any of these temperatures, including the ranges of 110° C.-115° C., 110° C.-120, 110° C.-125° C., 115° C.-120° C., 115° C.-125° C., 115° C.-130° C., 120° C.-125° C., 120° C.-130° C., and 125° C.-130° C.

Isolation of venetoclax crystalline form M9 may be carried out by methods well known and often used in the art, for example, by filtering the mixture to obtain a solid.

It is believed that venetoclax crystalline form M9 is anhydrous.

In another embodiment, venetoclax crystalline form M9 may be prepared by a process that includes the step of drying venetoclax crystalline form M22 at about 30° C. to about 80° C. for a time sufficient to produce the crystalline form M9. This includes temperatures of about 30, 35, 40° C., 45° C., 50° C., 55° C., 60° C., 65° C., 70° C., 75° C., 80° C., and between any of the aforementioned temperatures including the ranges of 30° C.-35° C., 30° C.-40° C., 30° C.-45° C., 30° C.-50° C., 30° C.-55° C., 30° C.-60° C., 30° C.-65° C., 30° C.-70° C., 30° C.-75° C., 30° C.-80° C., 35° C.-40° C., 35° C.-45° C., 35° C.-50° C., 35° C.-55° C., 35° C.-60° C., 35° C.-65° C., 35° C.-70° C., 35° C.-75° C., 35° C.-80° C., 40° C.-45° C., 40° C.-50° C., 40° C.-55° C., 40° C.-60° C., 40° C.-65° C., 40° C.-70° C., 40° C.-75° C., 40° C.-80° C., 45° C.-50° C., 45° C.-55° C., 45° C.-60° C., 45° C.-65° C., 45° C.-70° C., 45° C.-80° C., 50° C.-55° C., 55° C.-60° C., 55° C.-65° C., 55° C.-70° C., 55° C.-75° C., 55° C.-80° C., 60° C.-65° C., 60° C.-70° C., 60° C.-75° C., 60° C.-80° C., 65° C.-70° C., 65° C.-75° C., 65° C.-80° C., 70° C.-75° C., 70° C.-80° C., and 75° C.-80° C. For example, in some embodiments, venetoclax crystalline form M22 is dried at about 30° C. to about 80° C. under vacuum for about 46-50 hours to get venetoclax crystalline form M9.

Figure 10:
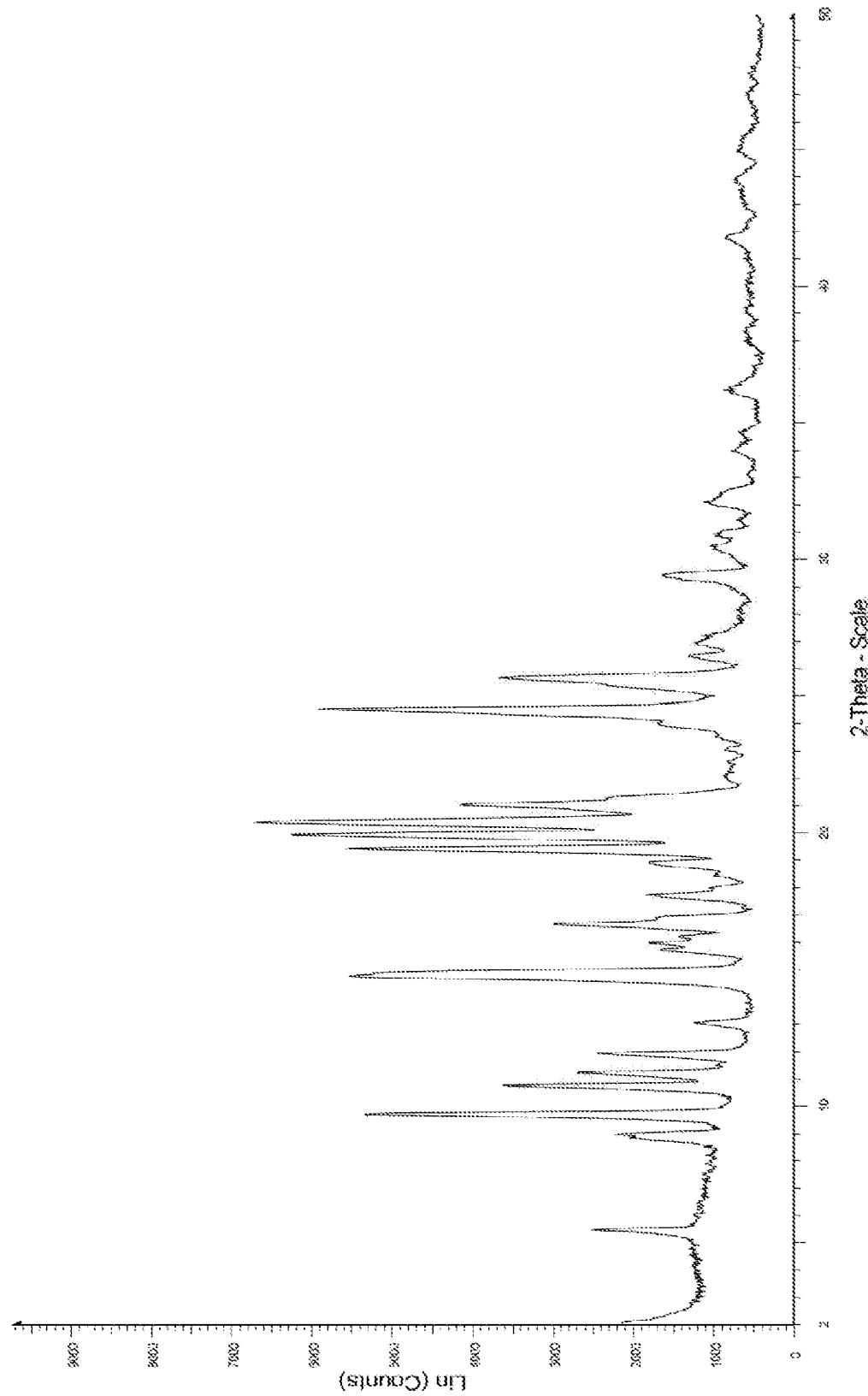
FIG. 10 is an X-ray powder diffractogram of venetoclax crystalline form M10.
Figure 25:
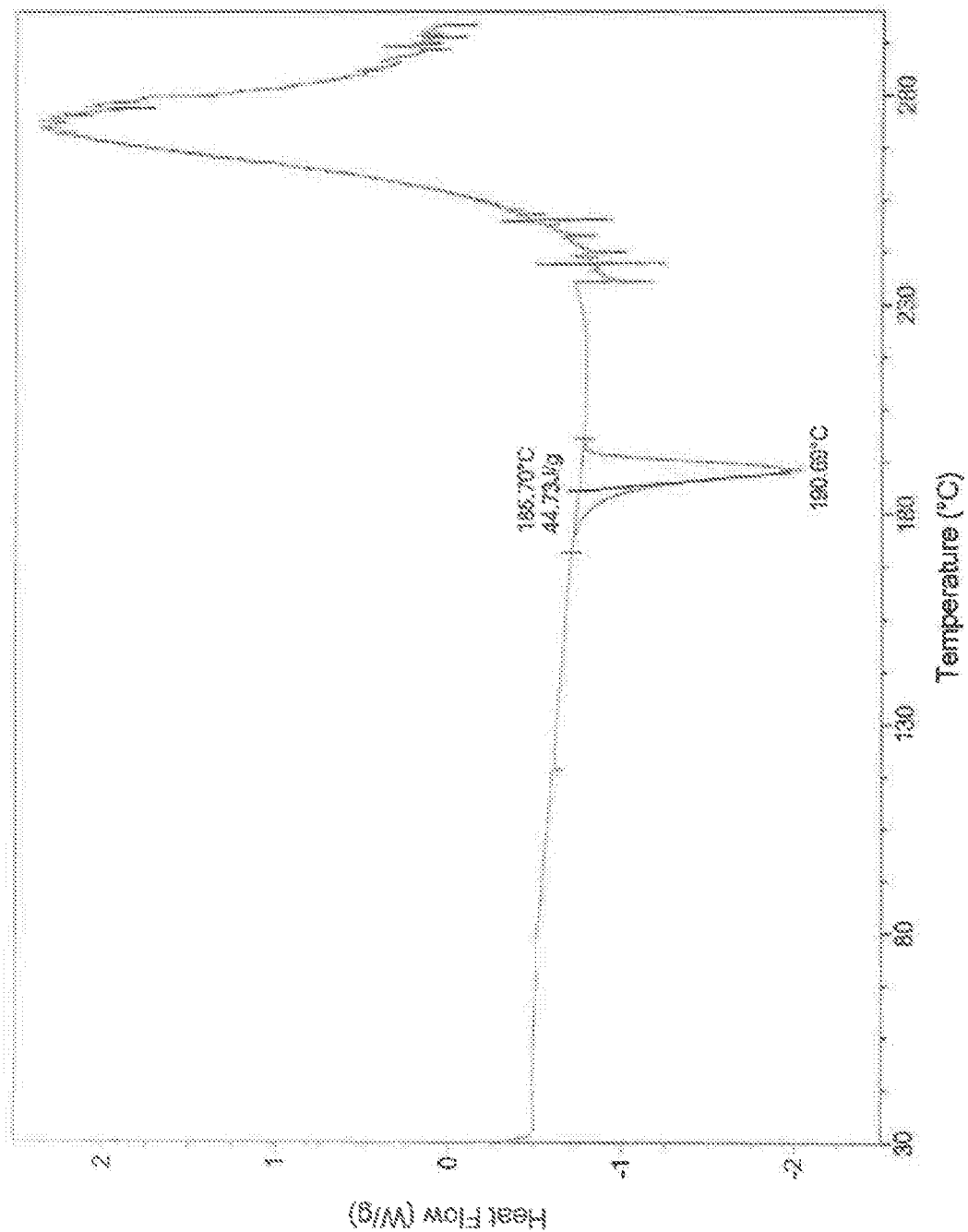
FIG. 25 is a DSC thermogram of venetoclax crystalline form M10.

In another aspect, the present invention provides venetoclax crystalline form M10, which may be characterized by a PXRD pattern having significant peaks at 2Θ angles of 19.38, 19.90, 20.36, and 24.50±0.2°. Venetoclax crystalline form M10 may be further characterized by a PXRD pattern having significant peaks at 2Θ angles of 5.38, 8.73, 8.88, 9.65, 10.68, 11.15, 11.86, 13.00, 14.74, 15.67, 15.93, 16.14, 16.61, 16.87, 17.67, 18.86, 19.38, 19.90, 20.36, 21.00, 21.25, 23.97, 24.50, 25.30, 25.63, 26.44, 26.91, 27.16, 29.39, and 32.07±0.2°. A representative PXRD pattern for venetoclax crystalline form M10 is shown in FIG. 10. A representative DSC thermogram of venetoclax crystalline form M10 is shown in FIG. 25.

In another aspect, the present invention provides a process for the preparation of venetoclax crystalline form M10. In one embodiment, venetoclax crystalline form M10 may be prepared by a process that includes the step of drying venetoclax crystalline form M4 at about 140° C. to 170° C. under vacuum for about 2 to about 4 hours.

Isolation of venetoclax crystalline form M10 may be carried out by methods well known and often used in the art, for example, by filtering the mixture to obtain a solid.

It is believed that venetoclax crystalline form M10 is anhydrous.

Figure 11:
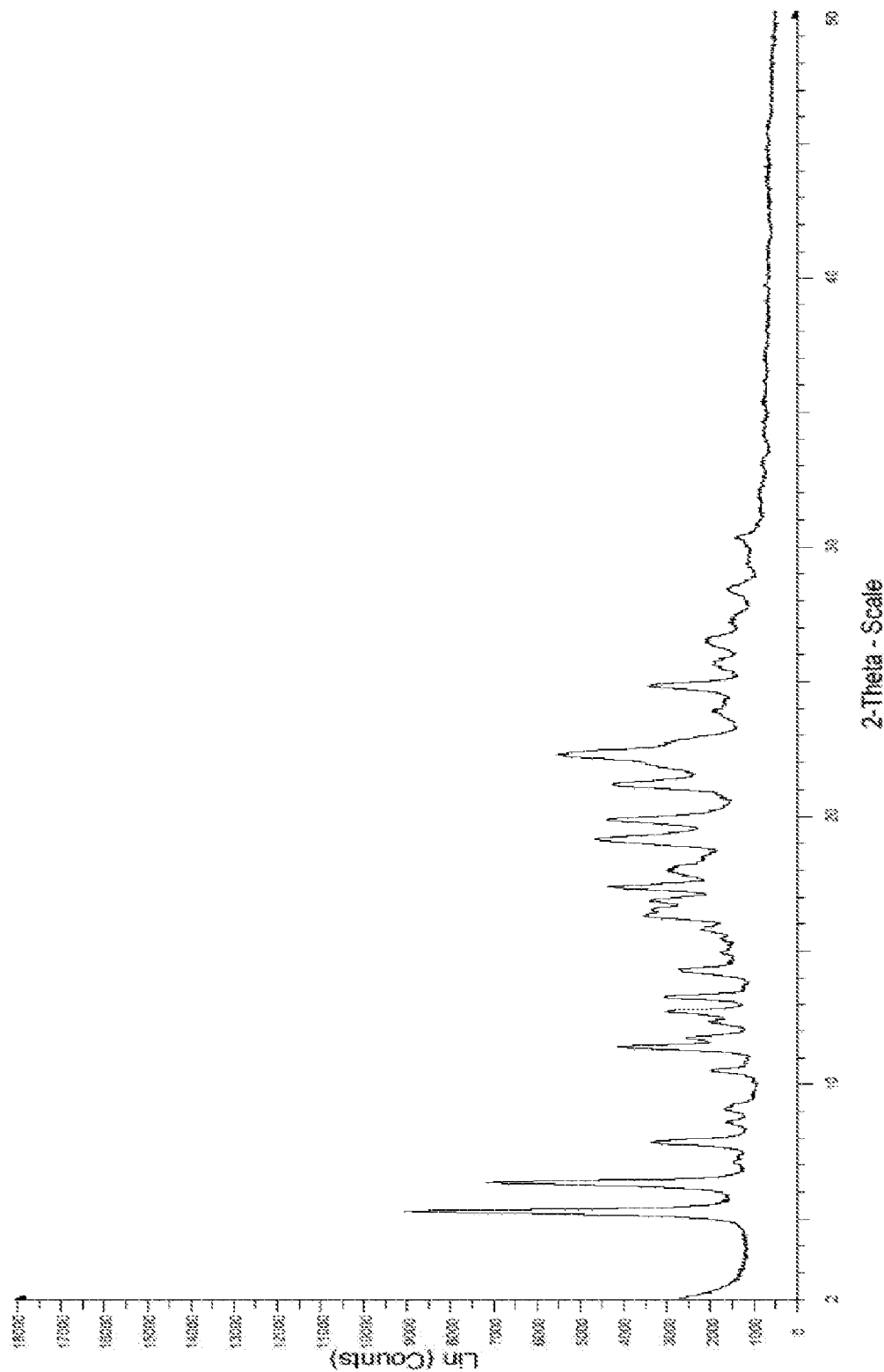
FIG. 11 is an X-ray powder diffractogram of venetoclax crystalline form M11.

In another embodiment, the present invention provides venetoclax crystalline form M11, which may be characterized by a PXRD pattern having significant peaks at 2Θ angles of 5.21, 6.29, 7.80, 10.47, 11.34, 11.67, 12.27, 12.66, 13.25, 14.23, 14.89, 15.43, 15.77, 16.27, 16.51, 16.83, 17.33, 17.96, 18.49, 19.10, 19.84, 21.16, 22.26, 22.73, 23.88, 24.83, 25.67, 26.55, 27.21, and 28.41±0.2°. A representative PX RD pattern for venetoclax crystalline form M11 is shown in FIG. 11.

In another aspect, the present invention provides a process for the preparation of venetoclax crystalline form M11. In one embodiment, venetoclax crystalline form M11 may be prepared by a process that includes the steps of:
 a) dissolving venetoclax in n-butyl acetate at about 70° C. to about 95° C. to form a solution;
 b) cooling the solution to about 15° C. to about 35° C.;
 c) optionally adding an anti-solvent; and
 d) isolating venetoclax crystalline form M11.

According to the present embodiment, venetoclax may be dissolved in n-butyl acetate at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70° C.-90° C., 75° C.-80° C., 75° C.-85° C., 75° C.-90° C., 75° C.-95° C., 80° C.-85° C., 80° C. 90° C., 80° C.-95° C., 85° C.-90° C., 85° C.-95° C., and 90° C.-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may then be added. Venetoclax crystalline form M11 may then be isolated.

Within the context of the present embodiment, the anti-solvent may be an ether, which may be, for example, methyl tert-butyl ether, diisopropyl ether, diethyl ether, or mixtures thereof.

Isolation of venetoclax crystalline form M11 may be carried out by methods well known and often used in the art, for example, by filtering the mixture to obtain a solid.

It is believed that venetoclax crystalline form M11 is an n-butyl acetate solvate.

Figure 12:
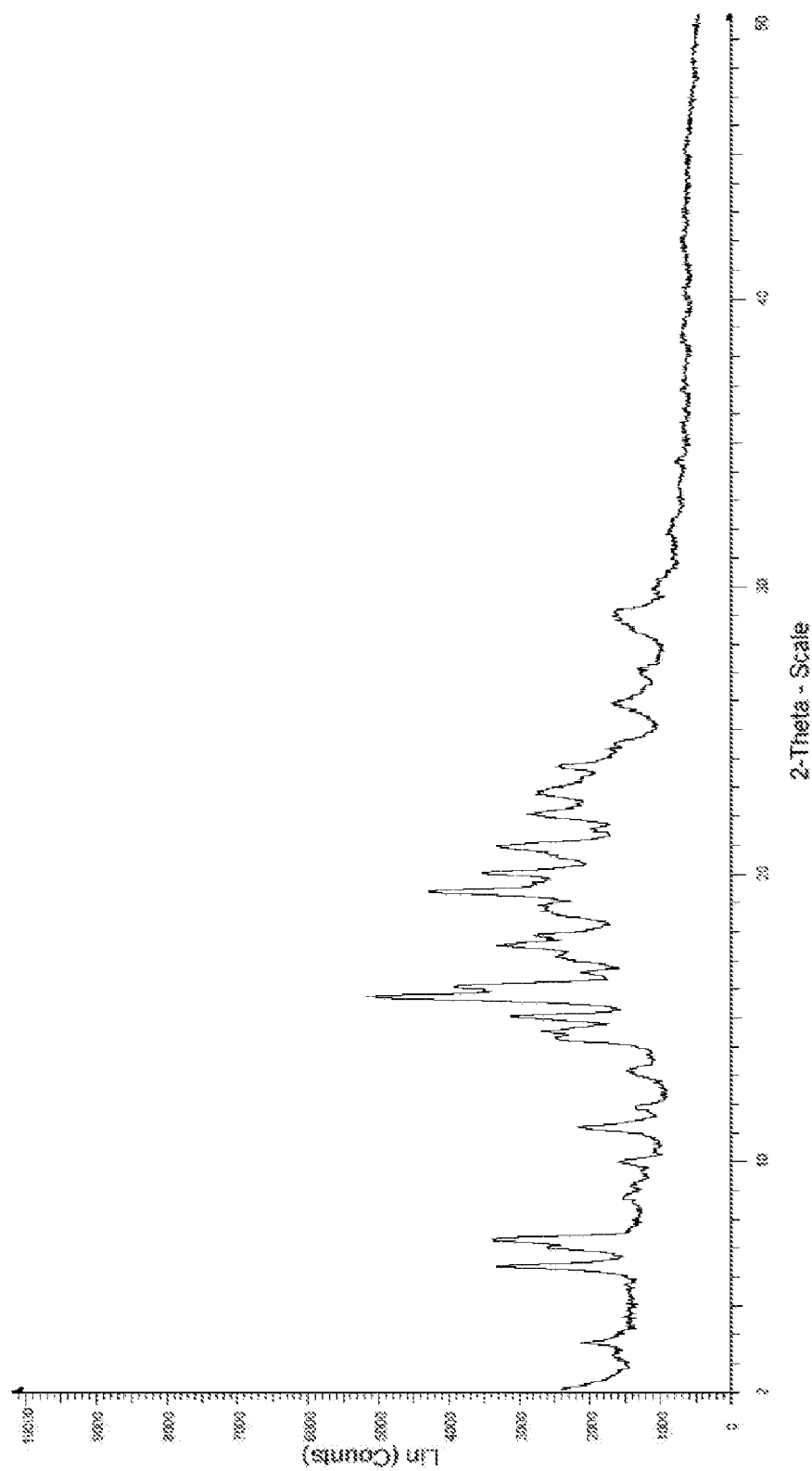
FIG. 12 is an X-ray powder diffractogram of venetoclax crystalline form M12.
Figure 13:
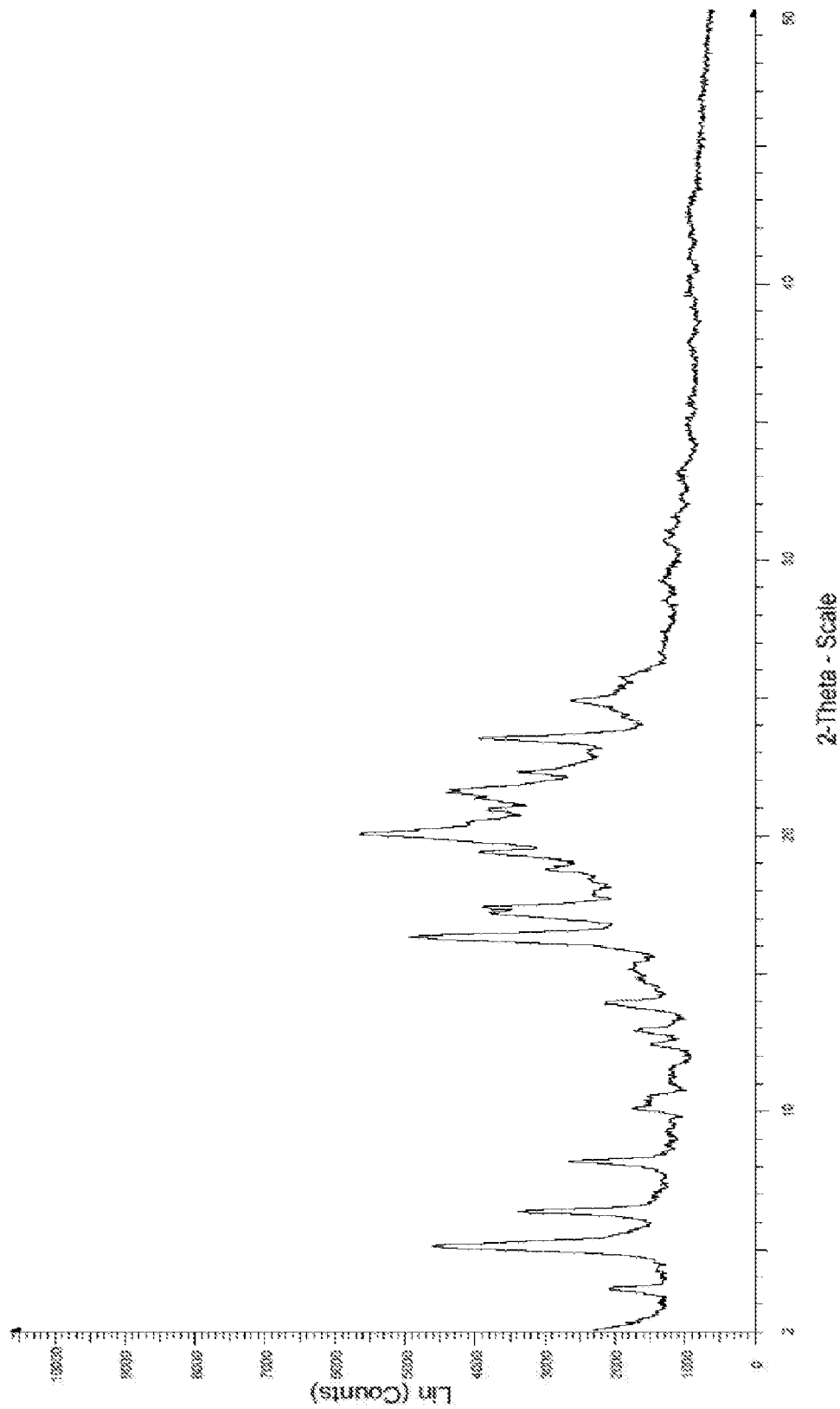
FIG. 13 is an X-ray powder diffractogram of venetoclax crystalline form M13.

In another embodiment, the present invention provides venetoclax crystalline form M12 which may be characterized by a PXRD pattern having significant peaks at 2Θ angles of 3.66, 6.32, 6.99, 7.24, 8.71, 9.94, 11.13, 11.86, 13.12, 14.23, 14.49, 15.00, 15.68, 16.04, 16.53, 17.09, 17.48, 17.81, 18.86, 19.34, 20.00, 20.92, 21.59, 22.04, 22.77, 23.71, 24.40, 25.90, 27.10, and 29.07±0.2°. A representative PXR D pattern for venetoclax crystalline form M12 is shown in FIG. 12.

In another aspect, the present invention provides a process for the preparation of venetoclax crystalline form M12. In one embodiment, venetoclax crystalline form M12 may be prepared by a process that includes the steps of:
 a) dissolving venetoclax in n-propyl acetate at about 70° C. to about 95° C. to form a solution;
 b) cooling the solution to about 15° C. to about 35° C.;
 c) optionally adding an anti-solvent; and
 d) isolating venetoclax crystalline form M12.

According to the present embodiment, venetoclax may be dissolved in n-propyl acetate at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70° C.-90° C., 75° C.-80° C., 75° C.-85° C., 75° C.-90° C., 75° C.-95° C., 80° C.-85° C., 80° C.-90° C., 80° C.-95° C., 85° C.-90° C., 85° C.-95° C., and 90-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may then be added. Venetoclax crystalline form M12 may then be isolated.

Within the context of the present embodiment, the anti-solvent is an ether, which may be, for example, methyl tert-butyl ether, diisopropyl ether, diethyl ether, or mixtures thereof.

Isolation of venetoclax crystalline form M12 may be carried out by methods well known and often used in the art, for example, by filtering the mixture to obtain a solid.

It is believed that venetoclax crystalline form M12 is an n-propyl acetate solvate.

In another embodiment, the present invention provides a novel crystalline form M13 of which may be characterized by a PXRD pattern having significant peaks at 2Θ angles of 3.49, 5.07, 6.32, 8.13, 10.05, 10.49, 12.37, 12.87, 13.89, 14.38, 14.73, 15.12, 16.30, 17.16, 17.35, 17.83, 18.41, 18.76, 19.37, 20.04, 20.90, 21.32, 21.57, 22.28, 23.04, 23.49, 24.88, 25.74, 28.52, 29.23, 30.72, and 31.03±0.2°. A representative PXRD pattern for venetoclax crystalline form M12 is shown in FIG. 12.

In another aspect, the present invention provides a process for the preparation of venetoclax crystalline form M13. In one embodiment, venetoclax crystalline form M13 may be prepared by a process that includes the steps of:
 a) dissolving venetoclax in 1-pentanol at about 70° C. to about 95° C. to form a solution;
 b) cooling the solution to about 15° C. to about 35° C.;
 c) optionally adding an anti-solvent; and
 d) isolating venetoclax crystalline form M13.

According to the present embodiment, venetoclax may be dissolved in 1-pentanol at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70° C.-90° C., 75° C.-80° C., 75° C.-85° C., 75° C.-90° C., 75° C.-95° C., 80° C.-85° C., 80° C.-90° C., 80° C.-95° C., 85° C.-90° C., 85° C.-95° C., and 90° C.-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may then be added. Venetoclax crystalline form M13 may then be isolated.

Within the context of the present embodiment, the anti-solvent is an ether, which may be, for example, methyl tert-butyl ether, diisopropyl ether, diethyl ether, or mixtures thereof.

Isolation of venetoclax crystalline form M13 may be carried out by methods well known and often used in the art, for example, by filtering the mixture to obtain a solid.

It is believed that venetoclax crystalline form M13 is a 1-pentanol solvate.

Figure 14:
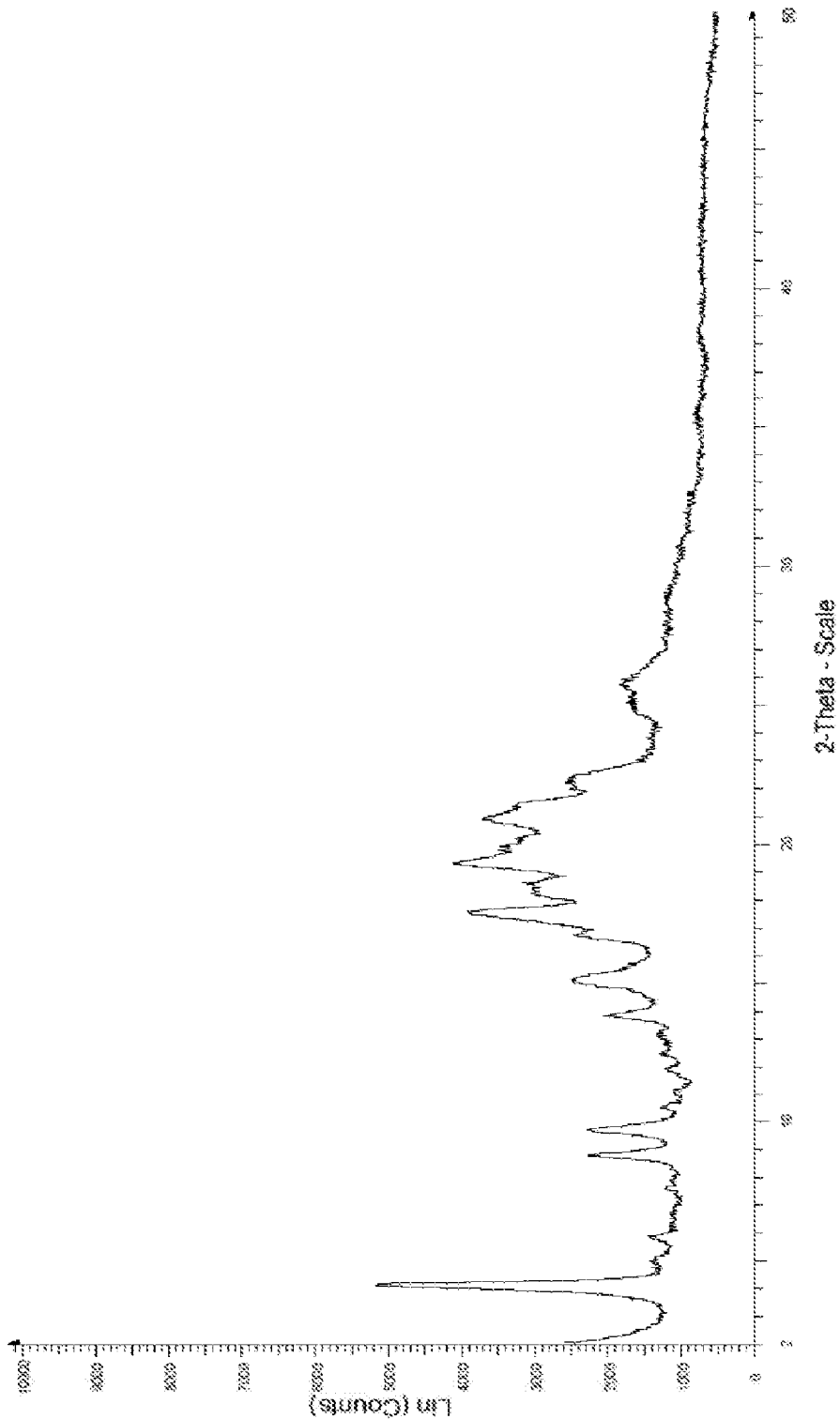
FIG. 14 is an X-ray powder diffractogram of venetoclax crystalline form M14.

In another embodiment, the present invention provides venetoclax crystalline form M14 which may be characterized by a PXRD pattern having significant peaks at 2Θ angles of 4.07, 8.75, 9.64, 13.16, 13.80, 15.08, 16.71, 17.51, 18.26, 18.61, 19.28, 19.90, 20.22, 20.89, 21.35, 22.26, 25.27, and 25.78±0.2°. A representative PXRD pattern for venetoclax crystalline form M14 is shown in FIG. 14.

In another aspect, the present invention provides a process for the preparation of venetoclax crystalline form M14. In one embodiment, venetoclax crystalline form M14 may be prepared by a process that includes the steps of:
 a) dissolving venetoclax in 2-butanol at about 70° C. to about 95° C. to form a solution;
 b) cooling the solution to about 15° C. to about 35° C.;
 c) optionally adding an anti-solvent; and
 d) isolating venetoclax crystalline form M14.

According to the present embodiment, venetoclax may be dissolved in 2-butanol at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70° C.-90° C., 75° C.-80° C., 75° C.-85° C., 75° C.-90° C., 75° C.-95° C., 80° C.-85° C., 80° C.-90° C., 80° C.-95° C., 85° C.-90° C., 85° C.-95° C., and 90° C.-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may then be added. Venetoclax crystalline form M14 may then be isolated.

Within the context of the present embodiment, the anti-solvent is an ether, which may be, for example, methyl tert-butyl ether, diisopropyl ether, diethyl ether, or mixtures thereof.

Isolation of venetoclax crystalline form M14 may be carried out by methods well known and often used in the art, for example, by filtering the mixture to obtain a solid.

It is believed that venetoclax crystalline form M14 is a 2-butanol solvate.

Figure 15:
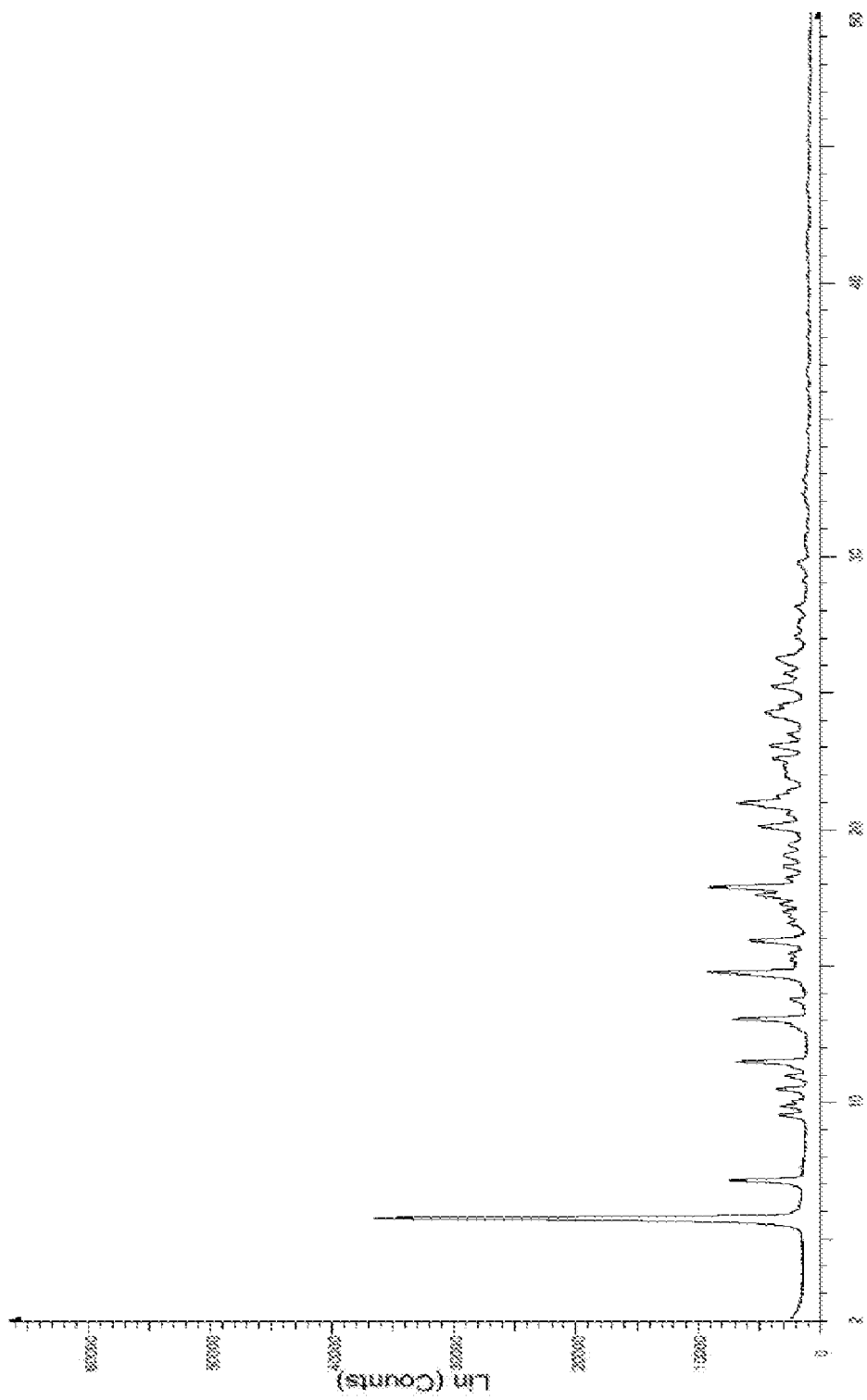
FIG. 15 is an X-ray powder diffractogram of venetoclax crystalline form M15.

In another embodiment, the present invention provides venetoclax crystalline form M15 which may be characterized by a PXRD pattern having significant peaks at 2Θ angles of 5.69, 7.09, 11.42, 12.99, 14.72, 15.89, 17.56, 17.85, 20.09, 20.92, and 24.26±0.2°. A representative PXRD pattern for venetoclax crystalline form M15 is shown in FIG. 15.

In another aspect, the present invention provides a process for the preparation of venetoclax crystalline form M15. In one embodiment, venetoclax crystalline form M15 may be prepared by a process that includes the steps of:
 a) dissolving venetoclax in 2-pentanone at about 70° C. to about 95° C. to form a solution;
 b) cooling the solution to about 15° C. to about 35° C.;
 c) optionally adding an anti-solvent; and
 d) isolating crystalline form M15 of venetoclax.

According to the present embodiment, venetoclax may be dissolved in 2-pentanone at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70° C.-90° C., 75° C.-80° C., 75° C.-85° C., 75° C.-90° C., 75° C.-95° C., 80° C.-85° C., 80° C.-90° C., 80° C.-95° C., 85° C.-90° C., 85° C.-95° C., and 90° C.-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 2 hours to about 3 hours. Optionally, an anti-solvent may then be added. Venetoclax crystalline form M15 may then be isolated.

Within the context of the present embodiment, the anti-solvent is a hydrocarbon, which may be, for example, pentane, hexane, cyclohexane, methyl cyclohexane, heptane, 2-methyl pentane, ethyl cyclohexane, or mixtures thereof.

Isolation of venetoclax crystalline form M15 may be carried out by methods well known and often used in the art, for example, by filtering the mixture to obtain a solid.

It is believed that venetoclax crystalline form M15 is a 2-pentanone solvate.

Figure 16:
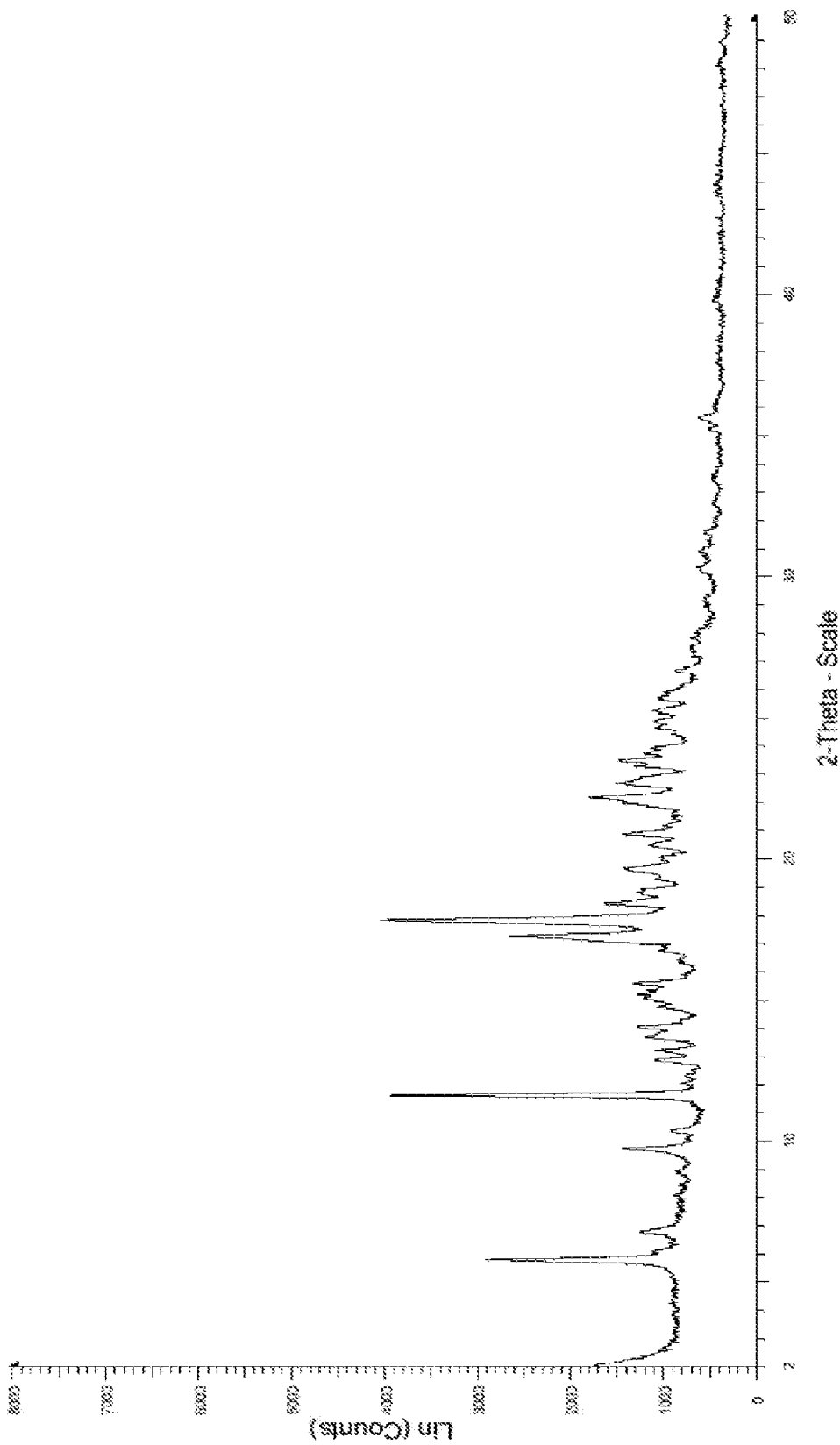
FIG. 16 is an X-ray powder diffractogram of venetoclax crystalline form M16.

In another embodiment, the present invention provides a venetoclax novel crystalline form M16 which may be characterized by a PXRD pattern having significant peaks at 2Θ angles of 5.73, 6.07, 6.74, 9.66, 11.58, 12.80, 13.17, 13.65, 13.99, 14.70, 15.02, 15.17, 15.54, 16.75, 17.23, 17.78, 18.38, 18.79, 19.24, 19.61, 20.04, 20.48, 20.86, 21.95, 22.16, 22.65, 23.28, 23.45, 23.72, 23.91, 24.61, 24.88, 25.23, 25.66, and 26.66±0.2°. A representative PXRD pattern for venetoclax crystalline form M16 is shown in FIG. 16.

In another aspect, the present invention provides a process for the preparation of venetoclax crystalline form M16. In one embodiment, venetoclax crystalline form M16 may be prepared by a process that includes the steps of:
 a) dissolving venetoclax in chlorobenzene at about 70° C. to about 95° C. to form a solution;
 b) cooling the solution to about 15° C. to about 35° C.;
 c) optionally adding an anti-solvent; and
 d) isolating venetoclax crystalline form M16.

According to the present embodiment, venetoclax may be dissolved in chlorobenzene at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70-90° C., 75° C.-80° C., 75° C.-85° C., 75° C.-90° C., 75° C.-95° C., 80° C.-85° C., 80° C.-90° C., 80° C.-95° C., 85° C.-90° C., 85° C.-95° C., and 90° C.-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 10 hours to about 14 hours. Optionally, an anti-solvent may then be added. Venetoclax crystalline form M16 may then be isolated.

Within the context of the present embodiment, the anti-solvent is an ether, which may be, for example, methyl tert-butyl ether, diisopropyl ether, diethyl ether, or mixtures thereof.

Isolation of venetoclax crystalline form M16 may be carried out by methods well known and often used in the art, for example, by filtering the mixture to obtain a solid.

It is believed that venetoclax crystalline form M16 is a chlorobenzene solvate.

Figure 17:
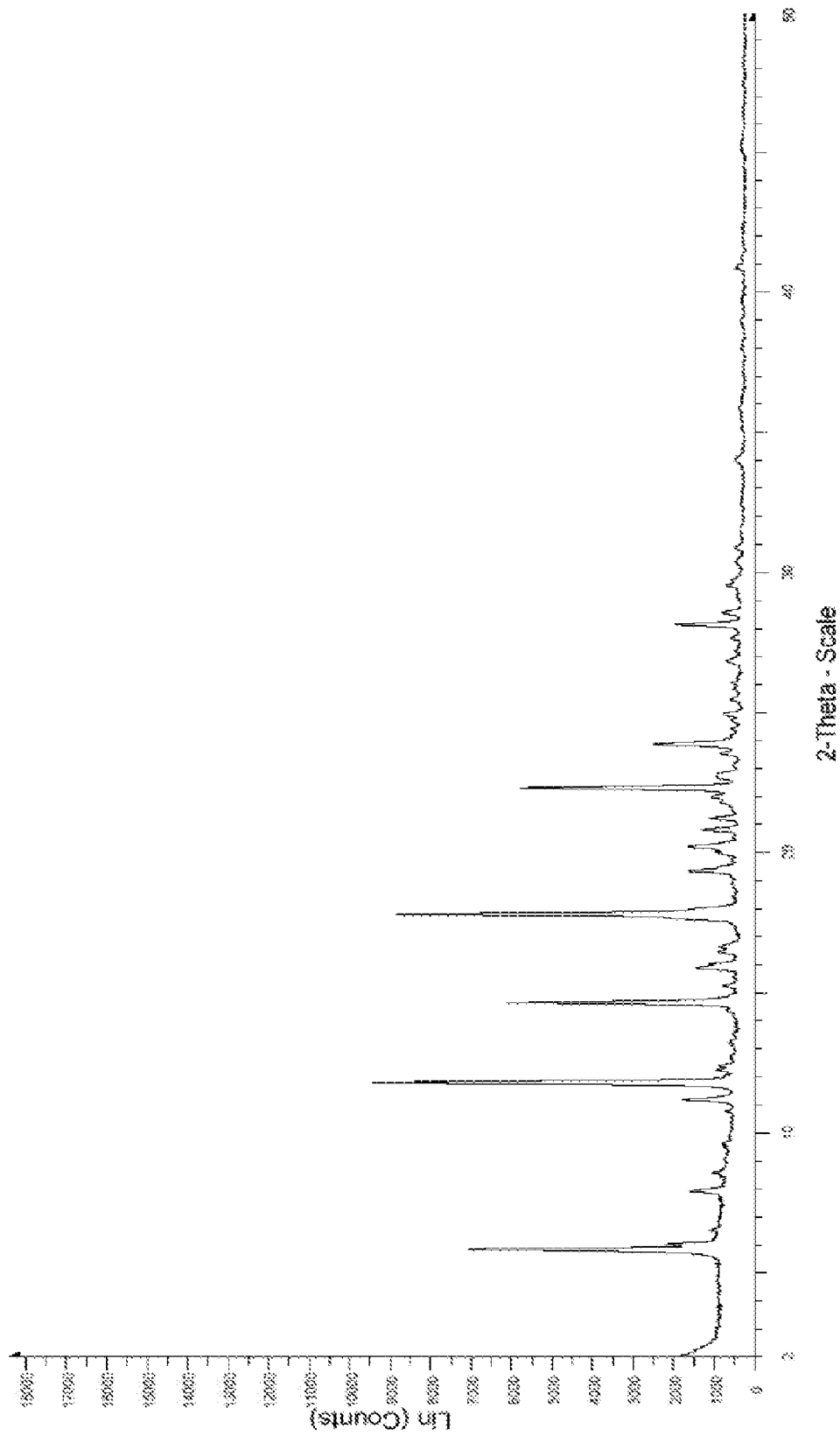
FIG. 17 is an X-ray powder diffractogram of venetoclax crystalline form M17.

In another embodiment, the present invention provides venetoclax crystalline form M17 which may be characterized by a PXRD pattern having significant peaks at 2Θ angles of 5.79, 5.98, 7.88, 11.16, 11.75, 14.61, 15.87, 17.79, 19.33, 20.20, 20.81, 22.30, 23.85, and 28.15±0.2°. A representative PXRD pattern for venetoclax crystalline form M17 is shown in FIG. 17.

In another aspect, the present invention provides a process for the preparation of venetoclax crystalline form M17. In one embodiment, venetoclax crystalline form M17 may be prepared by a process that includes the steps of:
 a) dissolving venetoclax in propionitrile at about 70° C. to about 95° C. to form a solution;
 b) cooling the solution to about 15° C. to about 35° C.;
 c) optionally adding an anti-solvent; and
 d) isolating venetoclax crystalline form M17.

According to the present invention, venetoclax may be dissolved in propionitrile at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70° C.-90° C., 75° C.-80° C., 75° C.-85° C., 75° C.-90° C., 75° C.-95° C., 80° C.-85° C., 80° C.-90° C., 80° C.-95° C., 85° C.-90° C., 85° C.-95° C., and 90° C.-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 10 hours to about 14 hours. Optionally, an anti-solvent may then be added. Venetoclax crystalline form M17 may then be isolated.

Within the context of the present embodiment, the anti-solvent is an ether, which may be, for example, methyl tert-butyl ether, diisopropyl ether, diethyl ether, or mixtures thereof.

Isolation of venetoclax crystalline form M17 may be carried out by methods well known and often used in the art, for example, by filtering the mixture to obtain a solid.

It is believed that venetoclax crystalline form M17 is a propionitrile solvate.

Figure 18:
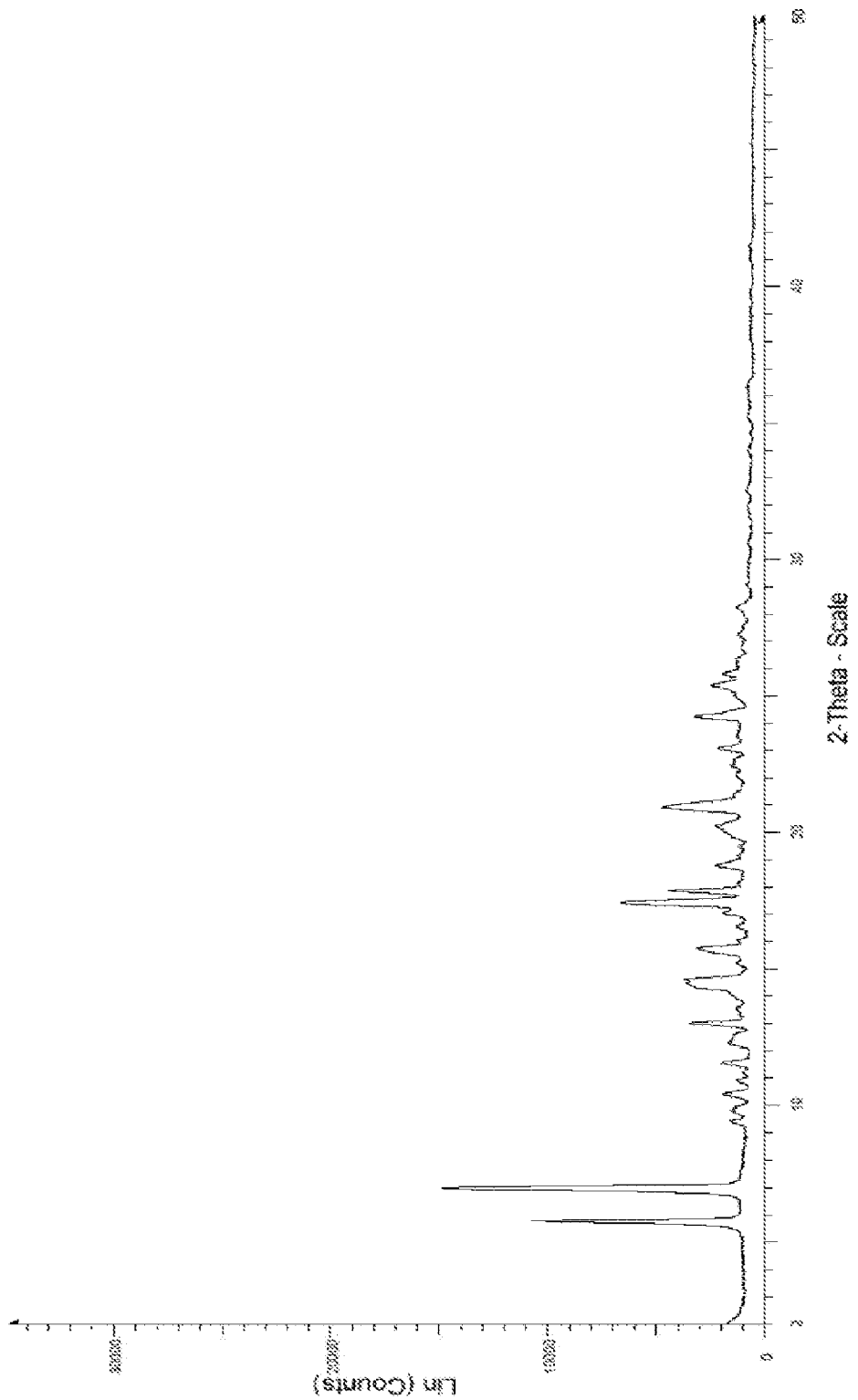
FIG. 18 is an X-ray powder diffractogram of venetoclax crystalline form M18.

In another embodiment, the present invention provides venetoclax crystalline form M18 which may be characterized by a PXRD pattern having significant peaks at 2Θ angles of 5.73, 6.93, 12.95, 14.53, 15.69, 17.39, 17.82, 18.77, 20.19, 20.90 23.07, 24.23 and 25.38±0.2°. A representative PXRD pattern for venetoclax crystalline form M18 is shown in FIG. 18.

In another aspect, the present invention provides a process for the preparation of venetoclax crystalline form M18. In one embodiment, venetoclax crystalline form M18 may be prepared by a process that includes the steps of:
 a) dissolving venetoclax in butyronitrile at about 70° C. to about 95° C. to form a solution;
 b) cooling the solution to about 15° C. to about 35° C.;
 c) optionally adding an anti-solvent; and
 d) isolating venetoclax crystalline form M18.

According to the present invention, venetoclax may be dissolved in butyronitrile at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70° C.-90° C., 75° C.-80° C., 75° C.-85° C., 75° C.-90° C., 75° C.-95° C., 80° C.-85° C., 80° C.-90° C., 80° C.-95° C., 85° C.-90° C., 85° C.-95° C., and 90° C.-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 10 hours to about 14 hours. Optionally, an anti-solvent may then be added. Venetoclax crystalline form M18 may then be isolated.

Within the context of the present embodiment, the anti-solvent may be an ether solvent, which may be, for example, methyl tert-butyl ether, diisopropyl ether, diethyl ether, or mixtures thereof.

Isolation of venetoclax crystalline form M18 may be carried out by methods well known and often used in the art, for example, by filtering the mixture to obtain a solid.

It is believed that venetoclax crystalline form M18 is a butyronitrile solvate.

Figure 19:
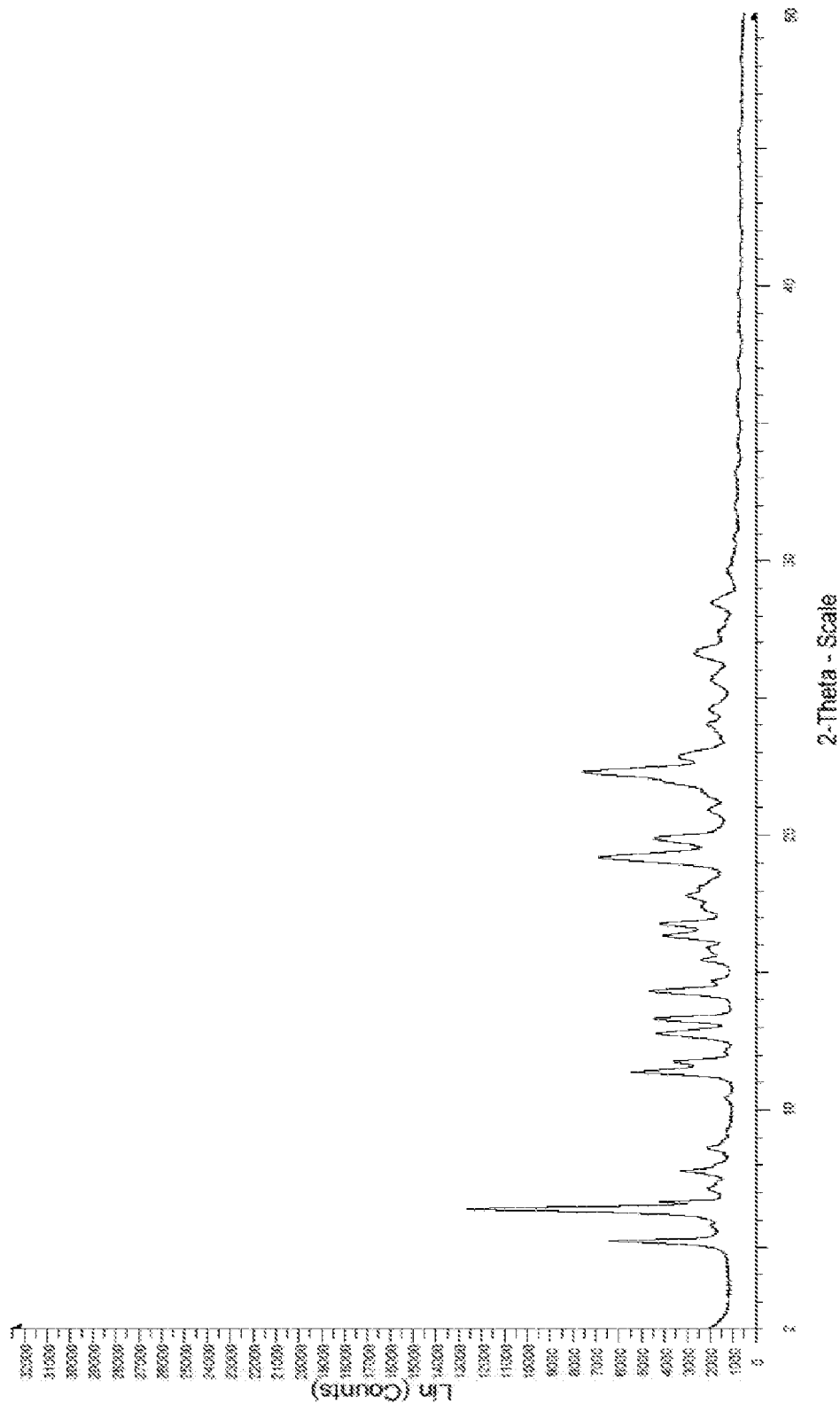
FIG. 19 is an X-ray powder diffractogram of venetoclax crystalline form M19.

In another embodiment, the present invention provides venetoclax crystalline form M19 characterized by a PXRD pattern having significant peaks at 2Θ angles of 5.18, 6.35, 6.60, 7.73, 11.34, 11.70, 12.73, 13.26, 14.26, 15.42, 15.82, 16.32, 16.75, 17.39, 17.78, 18.09, 19.17, 19.86, 20.91, 22.27, 22.84, 24.03, 24.55, 25.65, 26.57, and 28.48±0.2°. A representative PXRD pattern for venetoclax crystalline form M19 is shown in FIG. 19.

In another aspect, the present invention provides a process for the preparation of venetoclax crystalline form M19. In one embodiment, venetoclax crystalline form M19 may be prepared by a process that includes the steps of:
 a) dissolving venetoclax in isobutyronitrile at about 70° C. to about 95° C. to form a solution;
 b) cooling the solution to about 15° C. to about 35° C.;
 c) optionally adding an anti-solvent; and
 d) isolating crystalline form M19 of venetoclax.

According to the present embodiment, venetoclax may be dissolved in isobutyronitrile at about 70° C. to about 95° C. This range includes temperatures of 70° C., 75° C., 80° C., 85° C., 90° C., 95° C., and any temperature between any of those aforementioned, including 70° C.-75° C., 70° C.-80° C., 70° C.-85° C., 70° C.-90° C., 75° C.-80° C., 75° C.-85° C., 75° C.-90° C., 75° C.-95° C., 80° C.-85° C., 80° C.-90° C., 80° C.-95° C., 85° C.-90° C., 85° C.-95° C., and 90° C.-95° C. The solution may then be cooled to about 15° C. to about 35° C., which includes 15° C., 20° C., 25° C., 30° C., 35° C., and any temperature between any of those aforementioned including 15° C.-20° C., 15° C.-25° C., 15° C.-30° C., 20° C.-25° C., 20° C.-30° C., 20° C.-35° C., 25° C.-30° C., 25° C.-35° C., and 30° C.-35° C. In some embodiments, this cooling step is carried out for about 10 hours to about 14 hours. Optionally, an anti-solvent may then be added. Venetoclax crystalline form M19 may then be isolated.

Within the context of the present embodiment, the anti-solvent may be an ether solvent, which may be, for example, methyl tert-butyl ether, diisopropyl ether, diethyl ether, or mixtures thereof.

Isolation of venetoclax crystalline form M19 may be carried out by methods well known and often used in the art, for example, by filtering the mixture to obtain a solid.

It is believed that venetoclax crystalline form M19 is an isobutyronitrile solvate.

Figure 20:
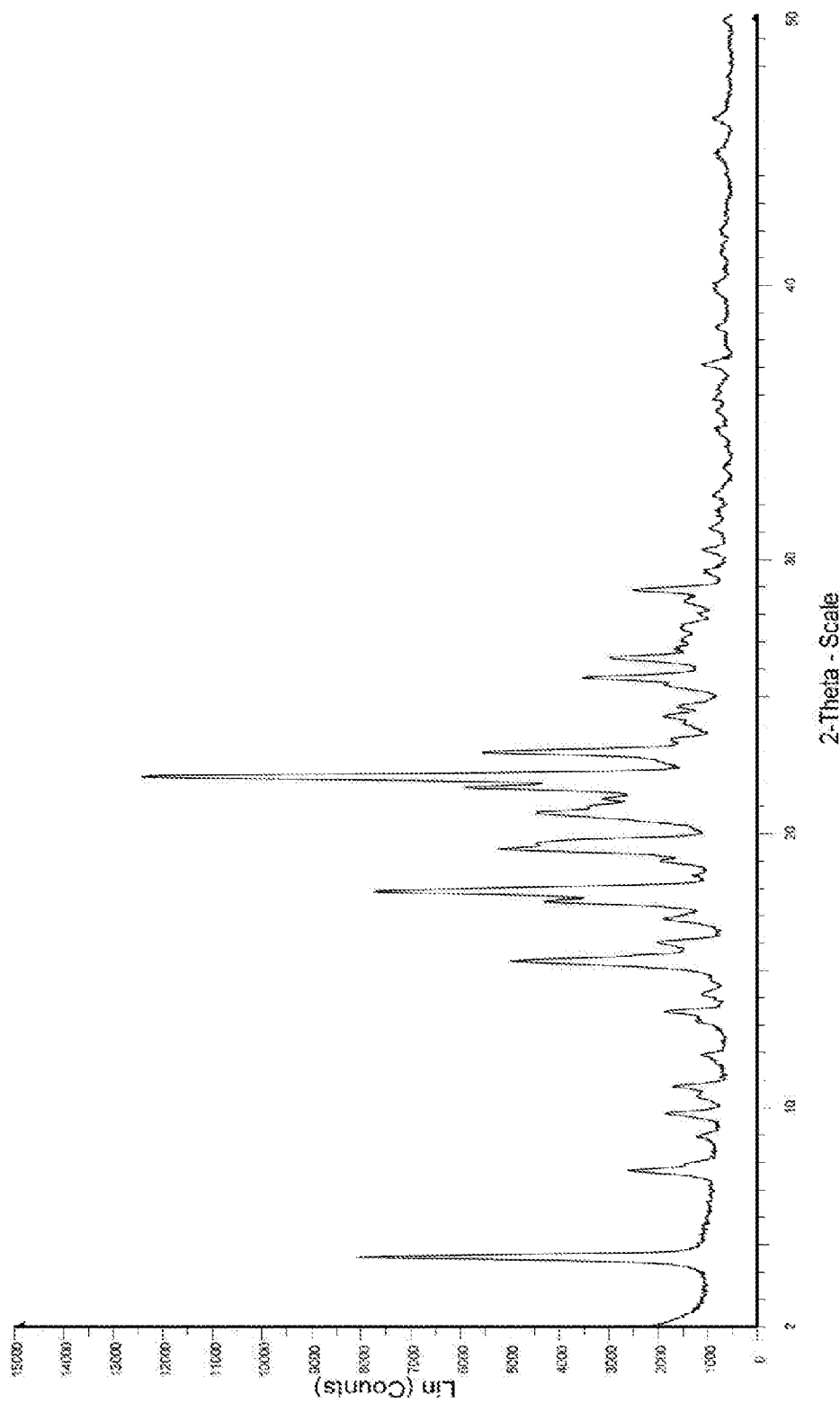
FIG. 20 is an X-ray powder diffractogram of venetoclax crystalline form M20.

In another embodiment, the present invention provides venetoclax crystalline form M20 characterized by a PXRD pattern having significant peaks at 2Θ angles of 4.48, 7.63, 13.46, 15.31, 15.98, 16.85, 17.49, 17.86, 18.97, 19.41, 19.60, 20.72, 21.27, 21.68, 22.06, 22.96, 23.40, 24.28, 25.36, 25.68, 26.39, and 28.88±0.2°. A representative PXRD pattern for venetoclax crystalline form M20 is shown in FIG. 20.

In another aspect, the present invention provides a process for the preparation of venetoclax crystalline form M20. In one embodiment, venetoclax crystalline form M20 may be prepared by a process that includes the steps of:
 a) dissolving venetoclax in anisole at about 80° C. to 105° C. to form a solution;
 b) cooling the solution to about 55° C. to 75° C.;
 c) optionally adding an anti-solvent; and
 d) isolating venetoclax crystalline form M20.

According to the present embodiment, venetoclax may be dissolved in anisole at about 80° C. to 105° C. This range includes temperatures of 80° C., 85° C., 90° C., 95° C., 100° C., 105° C., and any temperature between any of those aforementioned, including 80° C.-85° C., 80° C.-90° C., 80° C.-95° C., 80° C.-100° C., 85° C.-90° C., 85° C.-95° C., 85° C.-100° C., 85° C.-105° C., 90° C.-95° C., 90° C.-100° C., 90° C.-105° C., 95° C.-100° C., 95° C.-105° C., and 100° C.-105° C. The solution may then be cooled to about 55° C. to about 75° C., which includes 55° C., 60° C., 65° C., 70° C., 75° C., and any temperature between any of those aforementioned including 55° C.-60° C., 55° C.-65° C., 55° C.-70° C., 60° C.-65° C., 60° C.-70° C., 60° C.-75° C., 65° C.-70° C., 65° C.-75° C., and 70° C.-75° C. In some embodiments, this cooling step is carried out for about 2 hours to about 3 hours. Optionally, an anti-solvent may then be added. Venetoclax crystalline form M20 may then be isolated.

Within the context of the present embodiment, the anti-solvent is a hydrocarbon, which may be, for example, pentane, hexane, cyclohexane, methyl cyclohexane, heptane, or mixtures thereof.

Isolation of venetoclax crystalline form M20 may be carried out by methods well known and often used in the art, for example, by filtering the mixture to obtain a solid.

It is believed that venetoclax crystalline form M20 is an anisole solvate.

Figure 21:
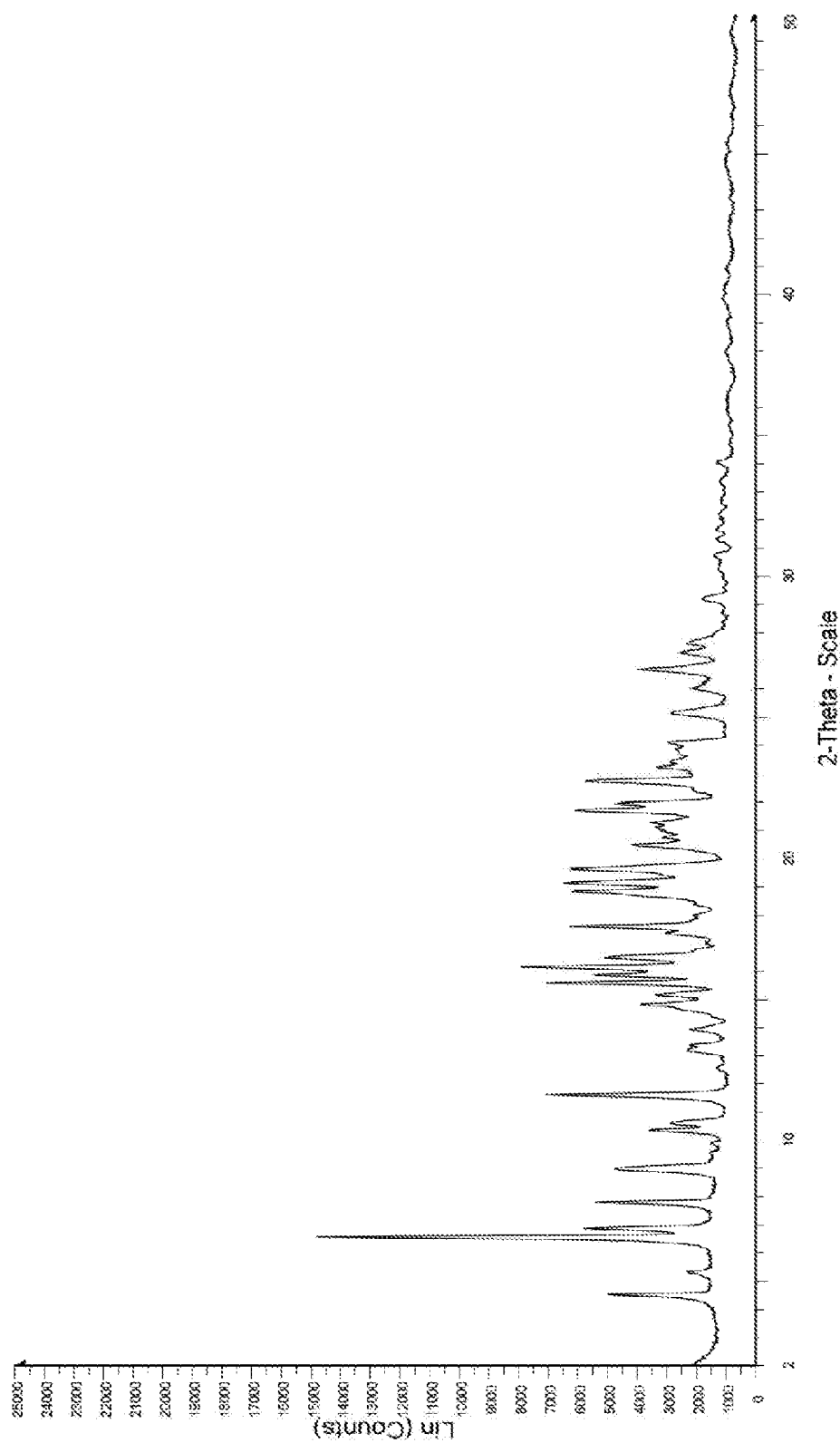
FIG. 21 is an X-ray powder diffractogram of venetoclax crystalline form M21.
Figure 26:
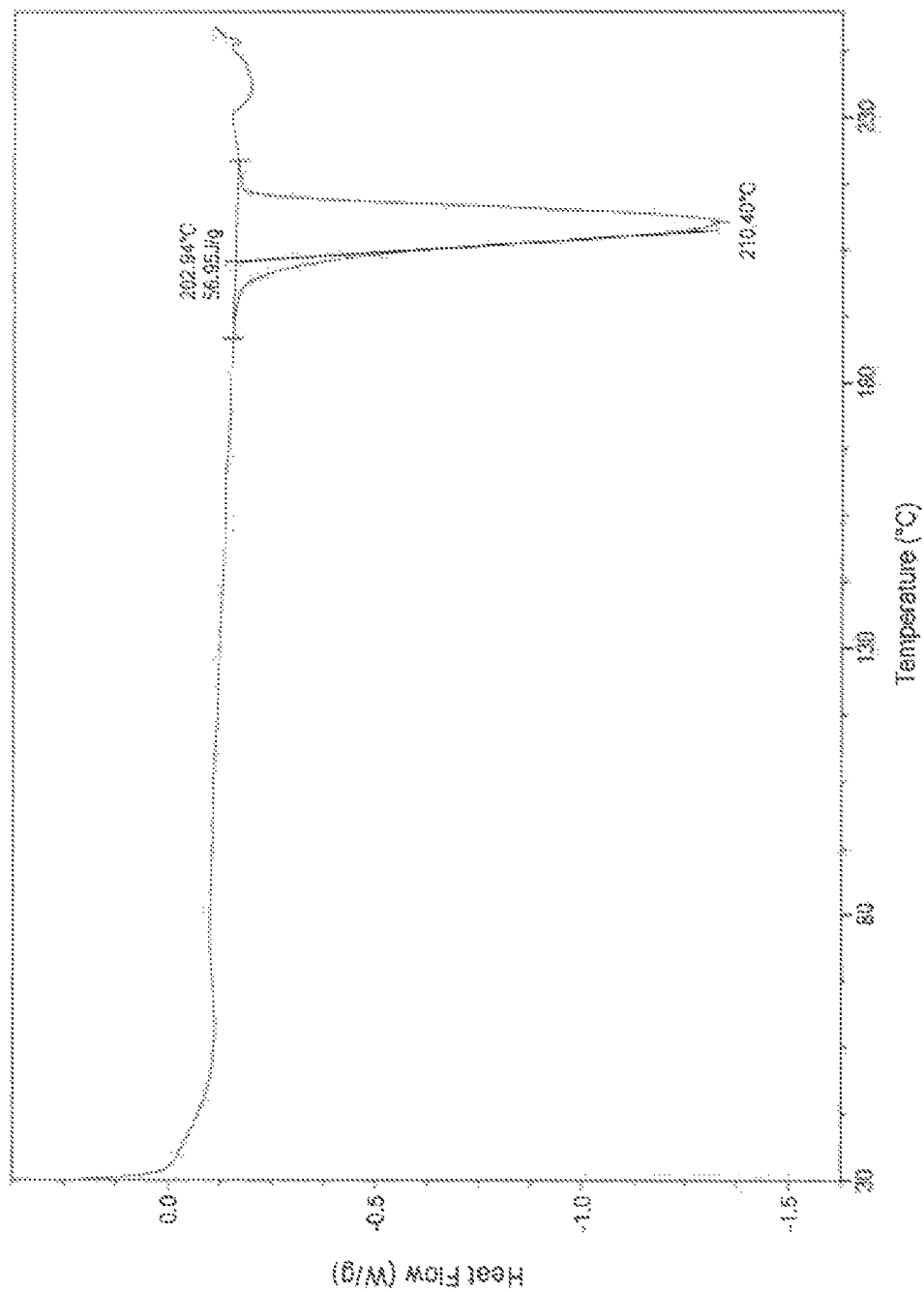
FIG. 26 is a DSC thermogram of venetoclax crystalline form M21.

In another aspect, the present invention provides venetoclax crystalline form M21 characterized by a PXRD pattern having significant peaks at 2Θ angles of 16.13, 18.80, 19.10, and 21.67±0.2°. Venetoclax crystalline form M21 may be further characterized by a PXRD pattern having significant peaks at 2Θ angles of 4.44, 5.22, 5.95, 6.52, 6.81, 7.72, 8.93, 10.33, 10.55, 11.54, 13.15, 13.91, 14.44, 14.74, 15.59, 15.87, 16.13, 16.41, 17.53, 18.80, 19.10, 19.47, 20.39, 21.04, 21.67, 22.68, 23.19, 23.72, 25.08, 26.05, 26.66, 27.24, 27.59, 29.15, 30.64, 31.41, 33.31, 34.01, 37.80, 39.72, 42.20, and 45.38±0.2°. A representative PXRD pattern for venetoclax crystalline form M21 is shown in FIG. 21. A representative DSC thermogram of venetoclax crystalline form M21 is shown in FIG. 26.

In another aspect, the present invention provides a process for the preparation of venetoclax crystalline form M21. In one embodiment, venetoclax crystalline form M21 may be prepared by a process that includes the steps of:
 a) dissolving venetoclax in an organic solvent at about 100° C. to 110° C. to form a solution;
 b) cooling the solution to about 65° C. to about 80° C.;
 c) optionally adding seeds of venetoclax form M21; and
 d) isolating venetoclax crystalline form M21.

According to the present embodiment, venetoclax may be dissolved in an organic solvent at about 100° C. to about 110° C. This range includes temperatures of 100° C., 102° C., 104° C., 106° C., 108° C., 110° C., and any temperature between any of those aforementioned, including 100° C.-102° C., 100° C.-104° C., 100° C.-106° C., 100° C.-108° C., 102° C.-104° C., 102° C.-106° C., 102° C.-108° C., 102° C.-110° C., 104° C.-106° C., 104° C.-108° C., 104° C.-110° C., 106° C.-108° C., 106° C.-110° C., and 108° C.-110° C. Within the context of this embodiment, the organic solvent may be, for example, toluene, n-butyl acetate, or mixtures thereof.

The solution may then be cooled to about 65° C. to about 80° C., which includes 65° C., 70° C., 75° C., 80° C., and any temperature between any of those aforementioned including 65° C.-70° C., 65° C.-75° C., 65° C.-80° C., 70° C.-75° C., 70° C.-80° C., and 75° C.-80° C. In some embodiments, this cooling step is carried out for about 4 hours to about 5 hours and optionally added seeds of venetoclax form M21 at the same temperature. Venetoclax crystalline form M21 may then be isolated.

Isolation of venetoclax crystalline form M21 may be carried out by methods well known and often used in the art, for example, by filtering the mixture to obtain a solid.

It is believed that venetoclax crystalline form M21 is anhydrous.

Figure 22:
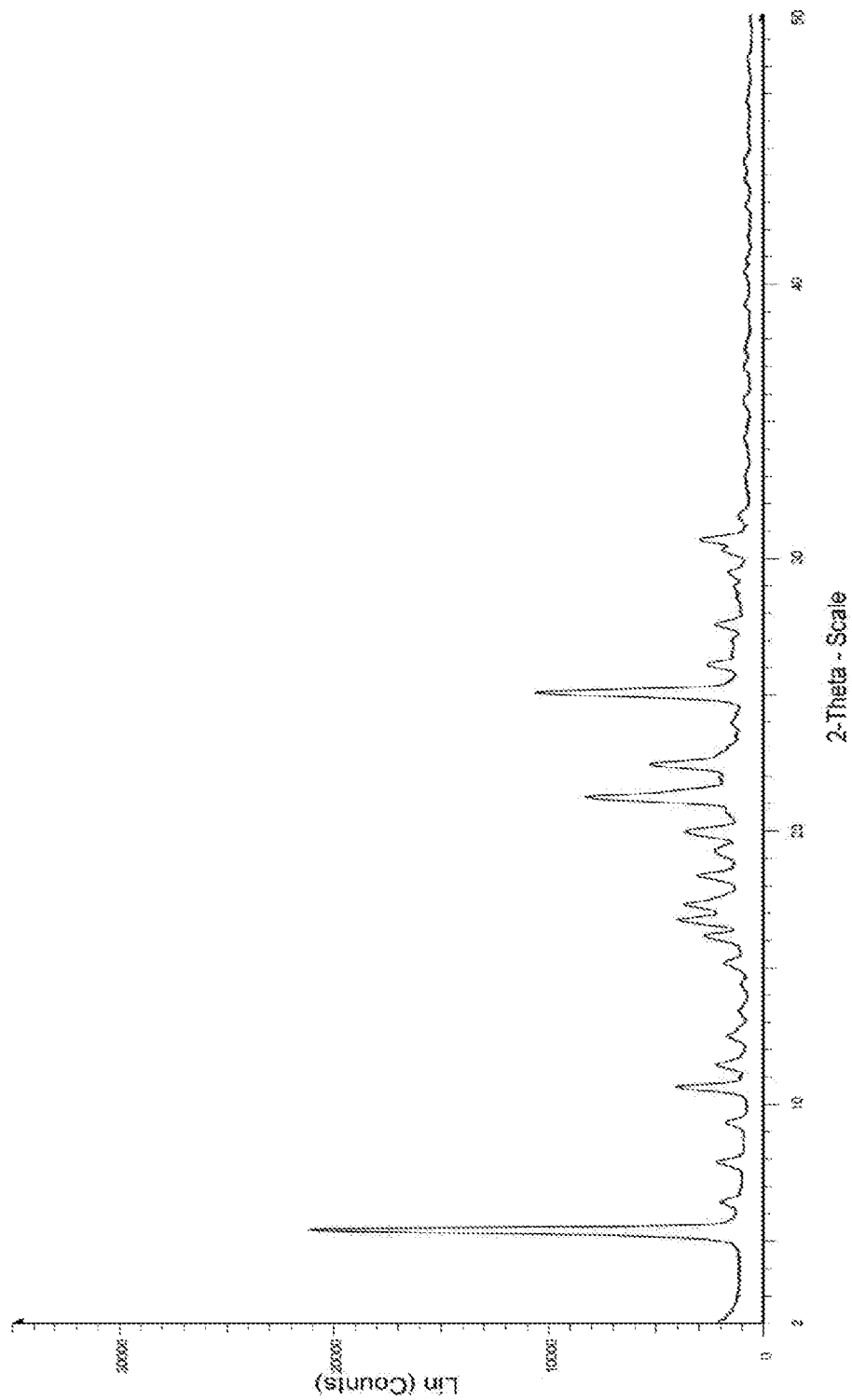
FIG. 22 is an X-ray powder diffractogram of venetoclax crystalline form M22.

In another embodiment, the present invention provides venetoclax crystalline form M22 characterized by a PXRD pattern having significant peaks at 2Θ angles of 5.33, 10.59, 16.14, 16.72, 17.29, 18.35, 19.97, 21.21, 22.44, 25.07, and 30.69±0.2°. A representative PXRD pattern for venetoclax crystalline form M22 is shown in FIG. 22.

In another aspect, the present invention provides a process for the preparation of venetoclax crystalline form M22. In one embodiment, venetoclax crystalline form M22 may be prepared by a process that includes the steps of:
 a) dissolving venetoclax in a mixture of toluene and anisole at about 100° C. to about 110° C. to form a solution;
 b) cooling the solution to about 65° C. to about 80° C.
 c) optionally adding an anti-solvent; and
 d) isolating venetoclax crystalline form M22.

According to the present embodiment, venetoclax may be combined with toluene at about 100° C. to about 110° C. This range includes temperatures of 100° C., 102° C., 104° C., 106° C., 108° C., 110° C., and any temperature between any of those aforementioned, including 100° C.-102° C., 100° C.-104° C., 100° C.-106° C., 100° C.-108° C., 102° C.-104° C., 102° C.-106° C., 102° C.-108° C., 102° C.-110° C., 104° C.-106° C., 104° C.-108° C., 104° C.-110° C., 106° C.-108° C., 106° C.-110° C., and 108° C.-110° C. Anisole may then be added to obtain a clear solution. The reaction mass may then be cooled to about 65° C. to about 80° C., which includes 65° C., 70° C., 75° C., 80° C., and any temperature between any of those aforementioned including 65° C.-70° C., 65° C.-75° C., 65° C.-80° C., 70° C.-75° C., 70° C.-80° C., and 75° C.-80° C. In some embodiments, this cooling step is carried out for about 2 to about 3 hours. Optionally, an anti-solvent may then be added. Venetoclax crystalline form M22 may then be isolated.

Within the context of this embodiment, the anti-solvent may be a hydrocarbon, which may be, for example, pentane, hexane, cyclohexane, methyl cyclohexane, heptane, 2-methyl pentane, ethyl cyclohexane, or mixtures thereof.

Isolation of venetoclax crystalline form M22 may be carried out by methods well known and often used in the art, for example, by filtering the mixture to obtain a solid.

It is believe that venetoclax crystalline form M22 is solvate of toluene and anisole.

According to the present invention, the table below lists the solvents that may be used to prepare the novel crystalline forms disclosed herein.

| Solvent | Crystalline form |
|---|---|
| Isobutyl acetate | M1 |
| Anisole | M2 |
| Acetonitrile | M3 |
| Toluene | M4 |
| 3-Pentanone | M5 |
| Dimethylformamide | M6 |
| Methyl ethyl ketone | M7 |
| Acetonitrile | M8 |
| n-butyl acetate | M11 |
| n-propyl acetate | M12 |
| 1-pentanol | M13 |
| 2-butanol | M14 |
| 2-pentanone | M15 |
| Chlorobenzene | M16 |
| Propionitrile | M17 |
| Butyronitrile | M18 |
| Isobutyronitrile | M19 |
| Anisole | M20 |
| Toluene &anisole | M22 |

Figure 23:
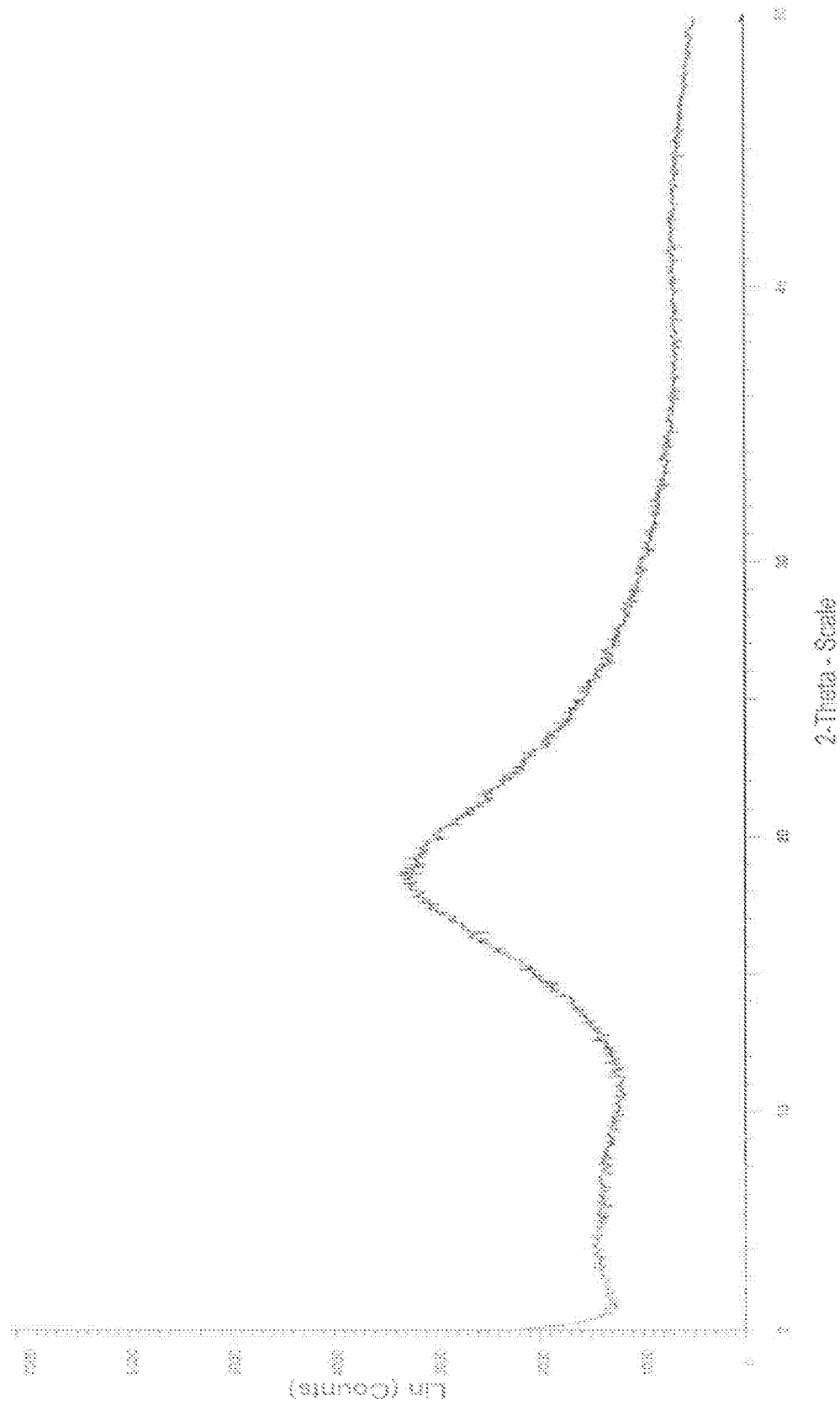
FIG. 23 is an X-ray powder diffractogram of an amorphous venetoclax.

In another aspect, the present invention provides a process for preparation of amorphous venetoclax. A representative PXRD pattern for amorphous venetoclax is shown in FIG. 23.

In one embodiment, amorphous venetoclax may be prepared by a process that includes the steps of:
a) dissolving venetoclax in an organic solvent to form a solution;
b) optionally combining the solution with an anti-solvent;
c) isolating amorphous venetoclax.

Within the context of this embodiment, venetoclax may be dissolved in an organic solvent to form a solution.

Within the context of this embodiment, the organic solvent is selected from dichloromethane, tetrahydrofuran, toluene, ethyl acetate, acetonitrile, acetone, dimethylformamide, dimethylsulfoxide, N-methylpyrrolidone, sulfolane, and mixtures thereof.

Optionally, the solution may be combined with an anti-solvent. Within the context of this embodiment, the anti-solvent is water.

Isolation of amorphous venetoclax may be carried out by methods well known and often used in the art, for example, by filtering the mixture to obtain a solid.

In another aspect, the present invention provides a process for the preparation of amorphous venetoclax, which includes the step of drying venetoclax crystalline form M20 at about 60° C. to about 80° C. for a time sufficient to produce the amorphous venetoclax.

For example, in some embodiments, venetoclax crystalline form M20 is dried at about 60° C. to about 80° C. under vacuum for about 14 hours to about 25 hours to get amorphous venetoclax.

According to the present invention, the starting material venetoclax in any one of the embodiments disclosed herein may be in crystalline or amorphous or semi-crystalline in nature and may be prepared as per the process disclosed in U.S. Pat. No. 8,546,399 or Indian provisional patent application No. 201641027658.

Some polymorphs of venetoclax disclosed herein may exhibit enhanced stability during storage. Thus, the stability of samples of amorphous venetoclax, as well as crystalline forms M9, M10, and M21 were stored at 40° C./75% relative humidity (RH) and at 25° C./60% relative humidity (RH) for 3 months. The samples were analyzed by PXRD for polymorph integrity.

Results of this testing revealed that amorphous venetoclax shows no change in PXRD pattern when stored for 3 months at 40° C./75% relative humidity (RH) and at 25° C./60% relative humidity (RH) conditions. Venetoclax crystalline form M9, M10, and M21 also shows no change in PXRD pattern when stored for 3 months at 40° C./75% relative humidity (RH) and at 25° C./60% relative humidity (RH) conditions. These results are shown in Table 1 below.

TABLE 1

| Time Point | Amorphous PXRD | M9 PXRD | M10 PXRD | M21 PXRD |
|---|---|---|---|---|
| at 40° C./75% RH | | | | |
| Initial | Amorphous | Crystalline | Crystalline | Crystalline |
| 15 days | Stable | Stable | Stable | Stable |
| 1 months | Stable | Stable | Stable | Stable |
| 2 months | Stable | Stable | Stable | Stable |
| 3 months | Stable | Stable | Stable | Stable |
| at 25° C./60% RH | | | | |
| Initial | Amorphous | Crystalline | Crystalline | Crystalline |
| 15 days | Stable | Stable | Stable | Stable |
| 1 months | Stable | Stable | Stable | Stable |
| 2 months | Stable | Stable | Stable | Stable |
| 3 months | Stable | Stable | Stable | Stable |

Within the context of the present invention, each disclosed form of venetoclax, (e.g., Forms M1, M2, M3, M4, M5, M6, M7, M8, M9, M10, M11, M12, M13, M14, M15, M16, M17, M18, M19, M20, M21, M22, as well as amorphous) may be useful in the formulation of a pharmaceutical dosage form as well as useful for the treatment of chronic lymphocytic leukemia with 17p deletion in patients that have received at least one prior therapy. Particularly useful dosage forms include oral dosage forms, for example, a tablet or capsule. Tablets or capsules may contain one or more inactive ingredients, including, for example, copovidone, colloidal silicon dioxide, polysorbate 80, sodium stearyl fumarate, and calcium phosphate dibasic. That tablet or capsule, in some embodiments, may be coated with a film that includes polyvinyl alcohol, polyethylene glycol, talc, titanium dioxide, and artificial colorings such as red ferric oxide, yellow ferric oxide, black ferric oxide, and inks, such as black ink.

Certain specific aspects and embodiments of the present application will be explained in greater detail with reference to the following examples, which are provided only for purposes of illustration and should not be construed as limiting the scope of the disclosure in any manner. Reasonable variations of the described procedures are intended to be within the scope of the present application. While particular aspects of the present application have been illustrated and described, it would be apparent to those skilled in the art that various other changes and modifications can be made without departing from the spirit and scope of the disclosure. It is therefore intended to encompass all such changes and modifications that are within the scope of this disclosure.

EXAMPLES

Example 1: Preparation of Venetoclax Crystalline Form M1

Venetoclax (0.3 g) was dissolved in isobutyl acetate (4.5 mL) at about 70° C., 80° C. The clear solution of venetoclax was cooled to about 20° C., 30° C., and maintained under stirring at 20° C., 30° C. for 2 hours. The solution was filtered and the obtained product was washed with methyl tert-butyl ether (1.5 mL) and suction dried for 30 minutes to yield venetoclax crystalline form M1.

Example 2: Preparation of Venetoclax Crystalline Form M2

Venetoclax (0.3 g) was dissolved in anisole (3 mL) at about 70° C., 80° C. The clear solution of venetoclax was cooled to about 20° C., 30° C., and maintained under stirring at 20° C., 30° C. for 2 hours. The solution was filtered and the obtained product was washed with heptane (0.5 mL) and suction dried for 30 minutes to yield venetoclax crystalline form M2.

Example 3: Preparation of Venetoclax Crystalline Form M3

Venetoclax (0.3 g) was dissolved in acetonitrile (3 mL) at about 70° C., 80° C. The clear solution of venetoclax was cooled to about 20° C., 30° C., and maintained under stirring at 20° C., 30° C. for 2 hours. The solution was filtered and the obtained product was washed with heptane (0.5 mL) and suction dried for 30 minutes to yield venetoclax crystalline form M3.

Example 4: Preparation of Venetoclax Crystalline Form M4

Venetoclax (0.3 g) was dissolved in toluene (6 mL) at about 70° C., 80° C. The clear solution of venetoclax was cooled to about 20° C., 30° C., and maintained under stirring at 20° C., 30° C. for 2 hours. The solution was filtered and the obtained product was washed with methyl tert-butyl ether (0.5 mL) and suction dried for 30 minutes to yield venetoclax crystalline form M4.

Example 5: Preparation of Venetoclax Crystalline Form M5

Venetoclax (0.3 g) was dissolved in 3-pentanone (3 mL) at about 70° C., 80° C. The clear solution of venetoclax was cooled to about 20° C., 30° C., and maintained under stirring at 20° C., 30° C. for 2 hours. The solution was filtered and the obtained product was washed with heptane (0.5 mL) and suction dried for 30 minutes to yield crystalline venetoclax 3-pentanone solvate form M5.

Example 6: Preparation of Venetoclax Crystalline Form M6

Venetoclax (0.3 g) was dissolved in dimethylformamide (3 mL) at about 70° C., 80° C. The clear solution of venetoclax was cooled to about 20° C., 30° C., and maintained under stirring at 20° C., 30° C. for 2 hours. The solution was filtered and the obtained product was washed with heptane (0.5 mL) and suction dried for 30 minutes to yield venetoclax crystalline form M6.

Example 7: Preparation of Venetoclax Crystalline Form M7

Venetoclax (0.3 g) was dissolved in methyl ethyl ketone (4.5 mL) at about 70° C., 80° C. The clear solution of venetoclax was cooled to about 20° C., 30° C., and maintained under stirring at 20° C., 30° C. for 2 hours. The solution was filtered and the obtained product was washed with methyl tert-butyl ether (0.5 mL) and suction dried for 30 minutes to yield crystalline venetoclax methyl ethyl ketone solvate form M7.

Example 8: Preparation of Venetoclax Crystalline Form M8

Venetoclax (13 g) was dissolved in acetonitrile (600 mL) at about 65-70° C. and stirred for 1 hour. The solution was filtered to remove any undissolved particulate at about 65-70° C. The clear solution of venetoclax was distilled on a rotary evaporator at 50° C., 55° C. until the total reaction volume was reduced to 65 mL. The reaction mass was then cooled to about 0° C., 5° C. and stirred for 4 hours. The solution was filtered and the obtained product was washed with acetonitrile (26 mL), and dried at 45-50° C. under vacuum for 3 hours to yield venetoclax crystalline form M8.

Example 9: Preparation of Venetoclax Crystalline Form M9

Crystalline venetoclax (3.5 g) form M1 was dried under vacuum at 125° C. for 2 hours. The resulting solid was identified as venetoclax crystalline form M9 (2.6 g).

Example 10: Preparation of Venetoclax Crystalline Form M10

Crystalline venetoclax (4.0 g) form M4 was dried under vacuum at 155° C. for 2 hours. The resulting solid was identified as venetoclax crystalline form M10 (3.2 g).

Example 11: Preparation of Venetoclax Crystalline Form M11

Venetoclax (0.3 g) was dissolved in n-butyl acetate (4.5 mL) at about 80° C., 90° C. The clear solution of venetoclax was cooled to about 20° C., 30° C., and maintained under stirring at 20° C., 30° C. for 2 hours. The solution was filtered and the obtained product was washed with methyl tert-butyl ether (0.6 mL) and suction dried for 30 minutes to yield venetoclax crystalline form M11 (0.25 g).

Example 12: Preparation of Venetoclax Crystalline Form M12

Venetoclax (0.3 g) was dissolved in n-propyl acetate (4.5 mL) at about 80° C., 90° C. The clear solution of venetoclax was cooled to about 20° C., 30° C., and maintained under stirring at 20° C., 30° C. for 2 hours. The solution was filtered and the obtained product was washed with methyl tert-butyl ether (0.6 mL) and suction dried for 30 minutes to yield venetoclax crystalline form M12 (0.23 g).

Example 13: Preparation of Venetoclax Crystalline Form M13

Venetoclax (0.3 g) was dissolved in 1-pentanol (3 mL) at about 80° C., 90° C. The clear solution of venetoclax was cooled to about 20° C., 30° C., and maintained under stirring at 20° C., 30° C. for 2 hours. The solution was filtered and the obtained product was washed with methyl tert-butyl ether (0.6 mL) and suction dried for 30 minutes to yield venetoclax crystalline form M13 (0.20 g).

Example 14: Preparation of Venetoclax Crystalline Form M14

Venetoclax (0.3 g) was dissolved in 2-butanol (3 mL) at about 80° C., 90° C. The clear solution of venetoclax was cooled to about 20° C., 30° C., and maintained under stirring at 20° C., 30° C. for 2 hours. The solution was filtered and the obtained product was washed with methyl tert-butyl ether (0.6 mL) and suction dried for 30 minutes to yield venetoclax crystalline form M14 (0.21 g).

Example 15: Preparation of Venetoclax Crystalline Form M15

Venetoclax (0.3 g) was dissolved in 2-pentanone (3 mL) at about 80° C., 90° C. The clear solution of venetoclax was cooled to about 20° C., 30° C., and maintained under stirring at 20° C., 30° C. for 2 hours. The solution was filtered and the obtained product was washed with heptane (0.6 mL) and suction dried for 30 minutes to yield venetoclax crystalline form M15 (0.24 g).

Example 16: Preparation of Venetoclax Crystalline Form M16

Venetoclax (0.3 g) was dissolved in chlorobenzene (2.1 mL) at about 80° C., 90° C. The clear solution of venetoclax was cooled to about 20° C., 30° C., and maintained under stirring at 20° C., 30° C. for 2 hours. The solution was filtered and the obtained product was washed with methyl tert-butyl ether (0.6 mL) and suction dried for 30 minutes to yield venetoclax crystalline form M16 (0.16 g).

Example 17: Preparation of Venetoclax Crystalline Form M17

Venetoclax (0.3 g) was dissolved in propionitrile (3.6 mL) at about 80° C., 90° C. The clear solution of venetoclax was cooled to about 20° C., 30° C., and maintained under stirring at 20° C., 30° C. for 12 hour s. The solution was filtered and the obtained product was washed with methyl tert-butyl ether (0.6 mL) and suction dried for 30 minutes to yield venetoclax crystalline form M17 (0.20 g).

Example 18: Preparation of Venetoclax Crystalline Form M18

Venetoclax (0.3 g) was dissolved in butyronitrile (3.6 mL) at about 80° C., 90° C. The clear solution of venetoclax was cooled to about 20° C., 30° C., and maintained under stirring at 20° C., 30° C. for 12 hour s. The solution was filtered and the obtained product was washed with methyl tert-butyl ether (0.6 mL) and suction dried for 30 minutes to yield venetoclax crystalline form M18 (0.17 g).

Example 19: Preparation of Venetoclax Crystalline Form M19

Venetoclax (0.3 g) was dissolved in isobutyronitrile (3.6 mL) at about 80° C., 90° C. The clear solution of venetoclax was cooled to about 20° C., 30° C., and maintained under stirring at 20° C., 30° C. for 12 hour s. The solution was filtered and the obtained product was washed with methyl tert-butyl ether (0.6 mL) and suction dried for 30 minutes to yield venetoclax crystalline form M19 (0.19 g).

Example 20: Preparation of Venetoclax Crystalline Form M20

Venetoclax (6 g) was dissolved in anisole (60 mL) at about 85-95° C. The clear solution of venetoclax was cooled to about 60° C., 70° C. and stirred at the same temperature for 3 hours. The solid obtained was filtered, washed with n-heptane (20 mL), and dried at 40° C. under vacuum for 5 hours. The product obtained was identified as venetoclax crystalline form M20 (3.5 g).

Example 21: Preparation of Venetoclax Crystalline Form M21

Venetoclax (1 g) and toluene (50 mL) were combined in a round bottomed flask. The reaction mass was heated to about 105-110° C. and stirred at the same temperature for 4 hours. The resultant slurry was cooled to 70° C. and stirred at the same temperature for 4 hours, after which it was further cooled to 25° C. and stirred at the same temperature for 15 hours. The solid obtained was filtered and dried at 40° C. under vacuum for 15 hours. The product obtained was identified as venetoclax crystalline form M21 (0.6 g).

Example 22: Preparation of Venetoclax Crystalline Form M21

Venetoclax (5 g) and toluene (200 mL) were combined in a round bottomed flask. The reaction mass was heated to about 105-110° C. and the resulting solution was cooled to 70° C., 80° C. Seeds of venetoclax form M21 (20 mg) were added at 70° C., 80° C. and the mixture was stirred for 18 hours at the same temperature. The solution was filtered and the obtained solid was dried at 70° C. under vacuum for 6 hours. The product obtained was identified as venetoclax crystalline form M21 (4.0 g).

Example 23: Preparation of Venetoclax Crystalline Form M21

Venetoclax (2 g) and n-butyl acetate (14 mL) were combined in round bottomed flask. The reaction mass was heated to 120° C., 130° C. and the resulting slurry was stirred at the same temperature for 3 hours. The slurry was then cooled to 70° C., heptane (30 mL) was added, and the mixture was stirred at the same temperature for 1 hour. The solution was hot filtered and the obtained solid was dried at 100° C., 110° C. under vacuum for 16 hours. The resulting pro duct obtained was identified as crystalline form M21 of Venetoclax. Yield: 1.6 g

Example 24: Preparation of Venetoclax Crystalline Form M22

Venetoclax (1.5 g) and toluene (60 mL) were combined in a round bottomed flask. The reaction mass was heated to about 105-110° C. Anisole (22 mL) was then added to the resulting slurry to obtain a clear solution which was further stirred for 4 hours at the same temperature. The reaction mass was cooled to about 70° C., n-heptane (30 mL) was added, and the mixture was stirred for 4 hours. The resulting slurry was cooled to about 25-30° C. and stirred at the same temperature for 15 hours. The solid obtained was filtered and suck-dried under vacuum for 10 minutes. The product obtained was identified as venetoclax crystalline form M22 (1.2 g).

Example 25: Preparation of Venetoclax Crystalline Form M9

Venetoclax form M22 (0.5 g) was dried at about 40° C., 70° C. under vacuum for 48 hours. The product obtained was identified as venetoclax crystalline form M9 (0.4 g).

Example 26: Preparation of Amorphous Venetoclax

Venetoclax (0.5 g) was dissolved in acetonitrile (25 mL) at about 80° C., 90° C. and stirred for 1 hour. The solution was filtered at 70° C. to remove any un-dissolved particulate. The clear solution was then distilled on a rotary evaporator at about 70° C., 75° C. until the total reaction volume was reduced to 20 mL. The concentrated reaction mass was then quenched and cooled to about 0° C., 5° C. in 10° C., 15 minutes and stirred for 30 minutes. The solution was filtered and the obtained solid was washed with methyl tert-butyl ether (5 mL) and dried at 30° C. under vacuum for 3 hours to yield amorphous venetoclax.

Example 27: Preparation of Amorphous Venetoclax

Venetoclax (7 g) was dissolved in dimethyl sulfoxide (28 mL) at about 25-30° C. The resulting clear solution was added to pre-cooled water (200 mL, 5° C.) for 10 minutes and stirred at the same temperature for 2 hours. The solution was filtered and the obtained solid was washed with water (21 mL) and dried at 60° C. under vacuum for 12 hours. The product obtained was identified as amorphous venetoclax (5.5 g).

Example 28: Preparation of Amorphous Venetoclax

Venetoclax (0.5 g) was dissolved in N,N-dimethylformamide (1 mL) at about 25-30° C. Chilled water was added to the clear solution and the mixture was stirred at about 25-30° C. for 15 hours. The solid obtained was filtered and dried at 40° C. under vacuum for 15 hours. The product obtained was identified as amorphous venetoclax (0.3 g).

Example 29: Preparation of Amorphous Venetoclax

Venetoclax form M20 (1.5 g) was dried at about 70° C. under vacuum for 15-24 hours. The product obtained was identified as amorphous venetoclax (1.2 g).

We claim:

1. Venetoclax crystalline form M21, characterized by a PXRD pattern having significant peaks at 2Θ angles of 16.13, 18.80, 19.10, and 21.67±0.2°.

2. A process for the preparation of venetoclax crystalline form M21 of claim 1, comprising the steps of:
   a. dissolving venetoclax in an organic solvent at about 100° C. to about 110° C. to form a solution, wherein the organic solvent is selected from the group consisting of N-butyl acetate, toluene, and mixtures thereof;
   b. cooling the solution to about 65° C. to about 80° C.;
   c. optionally adding seeds of venetoclax form M21; and
   d. isolating venetoclax crystalline form M21.

* * * * *